United States Patent [19]
Angeletti et al.

[11] Patent Number: 5,747,454
[45] Date of Patent: May 5, 1998

US005747454A

[54] CHROMOGRANIN PEPTIDES

[75] Inventors: Ruth Hogue Angeletti, New Rochelle; John Russell, Bronx, both of N.Y.

[73] Assignee: Albert Einstein College of Medicine of Yeshiva University, Bronx, N.Y.

[21] Appl. No.: 491,544

[22] Filed: Jun. 16, 1995

Related U.S. Application Data

[63] Continuation-in-part of Ser. No. 75,391, Jun. 9, 1993, Pat. No. 5,514,775.

[51] Int. Cl.$^6$ ............... A61K 38/00; C07K 5/00; C07K 7/00; C07K 16/00
[52] U.S. Cl. ............... 514/12; 530/324; 530/326
[58] Field of Search ............... 530/324, 326; 514/12

[56] References Cited

U.S. PATENT DOCUMENTS 5,514,775  5/1996  Hogue-Angeletti et al. ........... 530/326

OTHER PUBLICATIONS

Hogue-Angeletti, et al., Determination of Residues in Chromagranin A–(16–40) Required for Inhibition of Parathyroid Hormone Secretion, Endocrinology, 137(7), pp. 2918–2922, 1996.

*Primary Examiner*—Cecilia J. Tsang
*Assistant Examiner*—Jennifer Harle
*Attorney, Agent, or Firm*—Amster, Rothstein & Ebenstein

[57] ABSTRACT

This invention relates to synthetic chromogranin A peptides, pharmaceutical compositions comprising these peptides, and uses of the peptides for treating hyperparathyroidism, and treating or preventing conditions associated with hyperparathyroidism such as parathyroid hyperplasia-associated renal failure, osteoporosis, and the like.

17 Claims, No Drawings

CHROMOGRANIN PEPTIDES

CROSS REFERENCE TO RELATED APPLICATIONS

This Application is a continuation-in-part of application Ser. No. 08/075,391, filed Jun. 9, 1993, now U.S. Pat. No. 5,514,775, the contents of which is hereby incorporated by reference herein.

STATEMENT OF GOVERNMENT INTEREST

This invention was made with government support under NIH Grant Numbers NS 22697 and DK 34288. As such, the government has certain rights in the invention.

BACKGROUND OF THE INVENTION

Hyperparathyroidism is characterized by abnormally increased activity of the parathyroid gland resulting in increased production of parathyroid hormone. Excess of parathyroid hormone leads to alteration in function of cells of bone, renal tubules, and gastrointestinal mucosa, and may result in kidney stones and calcium deposits in renal tubules. Excess parathyroid hormone may also result in generalized decalcification of bone (osteoporosis), resulting in pain and tenderness of bones and spontaneous fractures, localized bone cysts, and hypercalcemia. Accordingly, there exists a need to inhibit excess parathyroid hormone secretion, and therefore effectively treat and prevent the complications associated with excess parathyroid secretion.

Chromogranin A (CGA) is a large, acidic protein found in the secretory granules of a wide variety of endocrine and neuroendocrine tissues including the parathyroid. Chromogranin A is present in relatively high concentrations in the parathyroid (see Takatsuki et al. *J. Biol. Chem.* 256: 2342–2345 (1981) and Cohn et al. *Biochemistry* 20:4135–4140 (1981)); and is co-secreted with parathyroid hormone in response to changes in extracellular calcium (see Cohn et al. *Endocrinology* 110:625–630 (1982)).

Although little is known about the function of chromogranins, there is a growing body of evidence that suggests that chromogranins may be precursors for a number of biologically active peptides. Chromogranin A was shown to inhibit parathyroid hormone secretion in primary cultures of parathyroid cells (see Fasciotto et al. *Endocrinology* 127:1329–1335 (1990)), and the amino terminal region of the protein was shown to be responsible for this activity (see Drees et al. *Endocrinology* 129:3381–3387 (1991)). Further, it was reported that amino terminal peptide $CGA_{1-40}$ stimulates secretion of the hormone CGRP and inhibits secretion of calcitonin (see Deftos et al. *J. Bone Min. Res.* 5:989–991 (1990)).

Copending application Ser. No. 08/075,391, filed Jun. 9, 1993, describes the synthesis and testing of chromogranin A peptides $CGA_{1-40}$ and $CGA_{17-38}$. Both peptides were shown to be effective in inhibiting parathyroid hormone secretion of bovine parathyroid cells.

The present invention provides additional chromogranin A peptides which are more soluble and biologically stable than the peptides described in copending application Ser. No. 08/075,391.

SUMMARY OF THE INVENTION

The present invention provides synthetic chromogranin A peptides capable of inhibiting parathyroid hormone secretion. The present invention also provides a pharmaceutical composition comprising a pharmaceutically acceptable carrier, and one or more of the chromogranin A peptides of the present invention and a pharmaceutically acceptable carrier. Finally, the present invention provides a method for inhibiting parathyroid hormone secretion which comprises administering to a subject a parathyroid hormone secretion inhibiting amount of one or more of the chromogranin A peptides of the present invention.

DETAILED DESCRIPTION OF THE INVENTION

The present invention provides a synthetic chromogranin A peptide having the amino acid sequence:
X-A-Ile-Val-Glu-Val-Ile-B-Asp-C-Leu-B-Lys-Pro-B-Pro -Met-Pro-Val-B-Lys-Glu-A-Y (SEQ ID NO:1),
wherein:
X is X1 or acetyl-X1, wherein X1 is:
Lys-,
Met-Lys-,
Val-Met-Lys-,
Glu-Val-Met-Lys-,
Thr-Glu-Val-Met-Lys-,
Asp-Thr-Glu-Val-Met-Lys-,
Gly-Asp-Thr-Glu-Val-Met-Lys-,
Lys-Gly-Asp-Thr-Glu-Val-Met-Lys-,
Asn-Lys-Gly-Asp-Thr-Glu-Val-Met-Lys-,
Met-Asn-Lys-Gly-Asp-Thr-Glu-Val-Met-Lys-, or
Pro-Met-Asn-Lys-Gly-Asp-Thr-Glu-Val-Met-Lys-,
A is Cys or lanthionine;
B is Ser or Ala;
C is Thr or Ala; and
Y is -Phe-Glu or -Phe-Glu-D-Thr.

In one embodiment of the present invention, the peptide has the amino acid sequence:
X-Cys-Ile-Val-Glu-Val-Ile-Ser-Asp-Thr-Leu-Ser -Lys-Pro- Ser-Pro-Met-Pro-Val-Ser-Lys-Glu-Cys-Y (SEQ ID NO:1),
wherein:
X is X1 or acetyl-X1, wherein X1 is:
Lys-,
Met-Lys-,
Val-Met-Lys-,
Glu-Val-Met-Lys-,
Thr-Glu-Val-Met-Lys-,
Asp-Thr-Glu-Val-Met-Lys-,
Gly-Asp-Thr-Glu-Val-Met-Lys-,
Lys-Gly-Asp-Thr-Glu-Val-Met-Lys-,
Asn-Lys-Gly-Asp-Thr-Glu-Val-Met-Lys-,
Met-Asn-Lys-Gly-Asp-Thr-Glu-Val-Met-Lys-, or
Pro-Met-Asn-Lys-Gly-Asp-Thr-Glu-Val-Met-Lys-; and
Y is -Phe-Glu or -Phe-Glu-D-Thr.

Representative peptides of the above peptide include but are not limited to the following peptides:

(a1) Lys-Cys-Ile-Val-Glu-Val-Ile-Ser-Asp-Thr-Leu-Ser-Lys -Pro-Ser-Pro-Met-Pro-Val-Ser-Lys-Glu-Cys-Phe-Glu (SEQ ID NO:1);

(a2) acetyl-Lys-Cys-Ile-Val-Glu-Val-Ile-Ser-Asp-Thr-Leu -Ser-Lys-Pro-Ser-Pro-Met-Pro-Val-Ser-Lys-Glu-Cys-Phe -Glu (SEQ ID NO:1);

(a3) Lys-Cys-Ile-Val-Glu-Val-Ile-Ser-Asp-Thr-Leu-Ser-Lys -Pro-Ser-Pro-Met-Pro-Val-Ser-Lys-Glu-Cys-Phe-Glu-D-Thr (SEQ ID NO:1);

(a4) acetyl-Lys-Cys-Ile-Val-Glu-Val-Ile-Ser-Asp-Thr-Leu -Ser-Lys-Pro-Ser-Pro-Met-Pro-Val-Ser-Lys-Glu-Cys-Phe -Glu-D-Thr (SEQ ID NO:1);

(b1) Met-Lys-Cys-Ile-Val-Glu-Val-Ile-Ser-Asp-Thr-Leu-Ser -Lys-Pro-Ser-Pro-Met-Pro-Val-Ser-Lys-Glu-Cys-Phe-Glu (SEQ ID NO:1);

(b2) acetyl-Met-Lys-Cys-Ile-Val-Glu-Val-Ile-Ser-Asp-Thr -Leu-Ser-Lys-Pro-Ser-Pro-Met-Pro-Val-Ser-Lys-Glu-Cys -Phe-Glu (SEQ ID NO:1);

(b3) Met-Lys-Cys-Ile-Val-Glu-Val-Ile-Ser-Asp-Thr-Leu-Ser -Lys-Pro-Ser-Pro-Met-Pro-Val-Ser-Lys-Glu-Cys-Phe- Glu -D-Thr (SEQ ID NO:1);

(b4) acetyl-Met-Lys-Cys-Ile-Val-Glu-Val-Ile-Ser-Asp-Thr -Leu-Ser-Lys-Pro-Ser-Pro-Met-Pro-Val-Ser-Lys-Glu-Cys -Phe-Glu-D-Thr (SEQ ID NO:1);

(c1) Val-Met-Lys-Cys-Ile-Val-Glu-Val-Ile-Ser-Asp-Thr-Leu -Ser-Lys-Pro-Ser-Pro-Met-Pro-Val-Ser-Lys-Glu-Cys-Phe -Glu (SEQ ID NO:1);

(c2) acetyl-Val-Met-Lys-Cys-Ile-Val-Glu-Val-Ile-Ser-Asp -Thr-Leu-Ser-Lys-Pro-Ser-Pro-Met-Pro-Val-Ser-Lys-Glu -Cys-Phe-Glu (SEQ ID NO:1);

(c3) Val-Met-Lys-Cys-Ile-Val-Glu-Val-Ile-Ser-Asp-Thr-Leu -Ser-Lys-Pro-Ser-Pro-Met-Pro-Val-Ser-Lys-Glu-Cys-Phe -Glu-D-Thr (SEQ ID NO:1);

(c4) acetyl-Val-Met-Lys-Cys-Ile-Val-Glu-Val-Ile-Ser-Asp -Thr-Leu-Ser-Lys-Pro-Ser-Pro-Met-Pro-Val-Ser-Lys-Glu -Cys-Phe-Glu-D-Thr (SEQ ID NO:1);

(d1) Glu-Val-Met-Lys-Cys-Ile-Val-Glu-Val-Ile-Ser-Asp-Thr -Leu-Ser-Lys-Pro-Ser-Pro-Met-Pro-Val-Ser-Lys-Glu-Cys -Phe-Glu (SEQ ID NO:1);

(d2) acetyl-Glu-Val-Met-Lys-Cys-Ile-Val-Glu-Val-Ile-Ser -Asp-Thr-Leu-Ser-Lys-Pro-Ser-Pro-Met-Pro-Val-Ser-Lys -Glu-Cys-Phe-Glu (SEQ ID NO:1);

(d3) Glu-Val-Met-Lys-Cys-Ile-Val-Glu-Val-Ile-Ser-Asp-Thr -Leu-Ser-Lys-Pro-Ser-Pro-Met-Pro-Val-Ser-Lys-Glu-Cys -Phe-Glu-D-Thr (SEQ ID NO:1);

(d4) acetyl-Glu-Val-Met-Lys-Cys-Ile-Val-Glu-Val-Ile-Ser -Asp-Thr-Leu-Ser-Lys-Pro-Ser-Pro-Met-Pro-Val-Ser-Lys -Glu-Cys-Phe-Glu-D-Thr (SEQ ID NO:1);

(e1) Thr-Glu-Val-Met-Lys-Cys-Ile-Val-Glu-Val-Ile-Ser-Asp -Thr-Leu-Ser-Lys-Pro-Ser-Pro-Met-Pro-Val-Ser-Lys-Glu -Cys-Phe-Glu (SEQ ID NO:1);

(e2) acetyl-Thr-Glu-Val-Met-Lys-Cys-Ile-Val-Glu-Val-Ile -Ser-Asp-Thr-Leu-Ser-Lys-Pro-Ser-Pro-Met-Pro-Val-Ser -Lys-Glu-Cys-Phe-Glu (SEQ ID NO:1);

(e3) Thr-Glu-Val-Met-Lys-Cys-Ile-Val-Glu-Val-Ile-Ser-Asp -Thr-Leu-Ser-Lys-Pro-Ser-Pro-Met-Pro-Val-Ser-Lys-Glu -Cys-Phe-Glu-D-Thr (SEQ ID NO:1);

(e4) acetyl-Thr-Glu-Val-Met-Lys-Cys-Ile-Val-Glu-Val-Ile -Ser-Asp-Thr-Leu-Ser-Lys-Pro-Ser-Pro-Met-Pro-Val-Ser -Lys-Glu-Cys-Phe-Glu-D-Thr (SEQ ID NO:1);

(f1) Asp-Thr-Glu-Val-Met-Lys-Cys-Ile-Val-Glu-Val-Ile-Ser -Asp-Thr-Leu-Ser-Lys-Pro-Ser-Pro-Met-Pro-Val-Ser-Lys -Glu-Cys-Phe-Glu (SEQ ID NO:1);

(f2) acetyl-Asp-Thr-Glu-Val-Met-Lys-Cys-Ile-Val-Glu-Val -Ile-Ser-Asp-Thr-Leu-Ser-Lys-Pro-Ser-Pro-Met-Pro-Val -Ser-Lys-Glu-Cys-Phe-Glu (SEQ ID No:1);

(f3) Asp-Thr-Glu-Val-Met-Lys-Cys-Ile-Val-Glu-Val-Ile-Ser -Asp-Thr-Leu-Ser-Lys-Pro-Ser-Pro-Met-Pro-Val-Ser-Lys -Glu-Cys-Phe-Glu-D-Thr (SEQ ID NO:1);

(f4) acetyl-Asp-Thr-Glu-Val-Met-Lys-Cys-Ile-Val-Glu-Val -Ile-Ser-Asp-Thr-Leu-Ser-Lys-Pro-Ser-Pro-Met-Pro-Val -Ser-Lys-Glu-Cys-Phe-Glu-D-Thr (SEQ ID NO:1);

(g1) Gly-Asp-Thr-Glu-Val-Met-Lys-Cys-Ile-Val-Glu-Val- Ile -Ser-Asp-Thr-Leu-Ser-Lys-Pro-Ser-Pro-Met-Pro-Val- Ser -Lys-Glu-Cys-Phe-Glu (SEQ ID NO:1);

(g2) acetyl-Gly-Asp-Thr-Glu-Val-Met-Lys-Cys-Ile-Val-Glu -Val-Ile-Ser-Asp-Thr-Leu-Ser-Lys-Pro-Ser-Pro-Met-Pro -Val-Ser-Lys-Glu-Cys-Phe-Glu (SEQ ID NO:1);

(g3) Gly-Asp-Thr-Glu-Val-Met-Lys-Cys-Ile-Val-Glu-Val- Ile -Ser-Asp-Thr-Leu-Ser-Lys-Pro-Ser-Pro-Met-Pro-Val- Ser -Lys-Glu-Cys-Phe-Glu-D-Thr (SEQ ID NO:1);

(g4) acetyl-Gly-Asp-Thr-Glu-Val-Met-Lys-Cys-Ile-Val-Glu -Val-Ile-Ser-Asp-Thr-Leu-Ser-Lys-Pro-Ser-Pro-Met-Pro -Val-Ser-Lys-Glu-Cys-Phe-Glu-D-Thr (SEQ ID NO:1);

(h1) Lys-Gly-Asp-Thr-Glu-Val-Met-Lys-Cys-Ile-Val-Glu- Val -Ile-Ser-Asp-Thr-Leu-Ser-Lys-Pro-Ser-Pro-Met-Pro- Val -Ser-Lys-Glu-Cys-Phe-Glu (SEQ ID NO:1);

(h2) acetyl-Lys-Gly-Asp-Thr-Glu-Val-Met-Lys-Cys-Ile-Val -Glu-Val-Ile-Ser-Asp-Thr-Leu-Ser-Lys-Pro-Ser-Pro-Met -Pro-Val-Ser-Lys-Glu-Cys-Phe-Glu (SEQ ID NO:1);

(h3) Lys-Gly-Asp-Thr-Glu-Val-Met-Lys-Cys-Ile-Val-Glu- Val -Ile-Ser-Asp-Thr-Leu-Ser-Lys-Pro-Ser-Pro-Met-Pro- Val -Ser-Lys-Glu-Cys-Phe-Glu-D-Thr (SEQ ID NO:1);

(h4) acetyl-Lys-Gly-Asp-Thr-Glu-Val-Met-Lys-Cys-Ile-Val -Glu-Val-Ile-Ser-Asp-Thr-Leu-Ser-Lys-Pro-Ser-Pro-Met -Pro-Val-Ser-Lys-Glu-Cys-Phe-Glu-D-Thr (SEQ ID NO:1);

(i1) Asn-Lys-Gly-Asp-Thr-Glu-Val-Met-Lys-Cys-Ile-Val- Glu -Val-Ile-Ser-Asp-Thr-Leu-Ser-Lys-Pro-Ser-Pro-Met- Pro -Val-Ser-Lys-Glu-Cys-Phe-Glu (SEQ ID NO:1);

(i2) acetyl-Asn-Lys-Gly-Asp-Thr-Glu-Val-Met-Lys-Cys-Ile -Val-Glu-Val-Ile-Ser-Asp-Thr-Leu-Ser-Lys-Pro-Ser-Pro -Met-Pro-Val-Ser-Lys-Glu-Cys-Phe-Glu (SEQ ID NO:1);

(i3) Asn-Lys-Gly-Asp-Thr-Glu-Val-Met-Lys-Cys-Ile-Val- Glu -Val-Ile-Ser-Asp-Thr-Leu-Ser-Lys-Pro-Ser-Pro-Met- Pro -Val-Ser-Lys-Glu-Cys-Phe-Glu-D-Thr (SEQ ID NO:1);

(i4) acetyl-Asn-Lys-Gly-Asp-Thr-Glu-Val-Met-Lys-Cys-Ile -Val-Glu-Val-Ile-Ser-Asp-Thr-Leu-Ser-Lys-Pro-Ser-Pro -Met-Pro-Val-Ser-Lys-Glu-Cys-Phe-Glu-D-Thr (SEQ ID NO:1);

(j1) Met-Asn-Lys-Gly-Asp-Thr-Glu-Val-Met-Lys-Cys-Ile- Val -Glu-Val-Ile-Ser-Asp-Thr-Leu-Ser-Lys-Pro-Ser-Pro- Met -Pro-Val-Ser-Lys-Glu-Cys-Phe-Glu (SEQ ID NO:1);

(j2) acetyl-Met-Asn-Lys-Gly-Asp-Thr-Glu-Val-Met-Lys- Cys -Ile-Val-Glu-Val-Ile-Ser-Asp-Thr-Leu-Ser-Lys-Pro- Ser -Pro-Met-Pro-Val-Ser-Lys-Glu-Cys-Phe-Glu (SEQ ID NO:1);

(j3) Met-Asn-Lys-Gly-Asp-Thr-Glu-Val-Met-Lys-Cys-Ile- Val -Glu-Val-Ile-Ser-Asp-Thr-Leu-Ser-Lys-Pro-Ser-Pro- Met -Pro-Val-Ser-Lys-Glu-Cys-Phe-Glu-D-Thr (SEQ ID NO:1);

(j4) acetyl-Met-Asn-Lys-Gly-Asp-Thr-Glu-Val-Met-Lys- Cys -Ile-Val-Glu-Val-Ile-Ser-Asp-Thr-Leu-Ser-Lys-Pro- Ser -Pro-Met-Pro-Val-Ser-Lys-Glu-Cys-Phe-Glu-D-Thr (SEQ ID NO:1);

(k1) Pro-Met-Asn-Lys-Gly-Asp-Thr-Glu-Val-Met-Lys-Cys- Ile -Val-Glu-Val-Ile-Ser-Asp-Thr-Leu-Ser-Lys-Pro-Ser- Pro -Met-Pro-Val-Ser-Lys-Glu-Cys-Phe-Glu (SEQ ID NO:1);

(k2) acetyl-Pro-Met-Asn-Lys-Gly-Asp-Thr-Glu-Val-Met- Lys -Cys-Ile-Val-Glu-Val-Ile-Ser-Asp-Thr-Leu-Ser-Lys- Pro -Ser-Pro-Met-Pro-Val-Ser-Lys-Glu-Cys-Phe-Glu (SEQ ID NO:1);

(k3) Pro-Met-Asn-Lys-Gly-Asp-Thr-Glu-Val-Met-Lys-Cys- Ile -Val-Glu-Val-Ile-Ser-Asp-Thr-Leu-Ser-Lys-Pro-Ser- Pro -Met-Pro-Val-Ser-Lys-Glu-Cys-Phe-Glu-D-Thr (SEQ ID NO:1);

(k4) acetyl-Pro-Met-Asn-Lys-Gly-Asp-Thr-Glu-Val-Met- Lys -Cys-Ile-Val-Glu-Val-Ile-Ser-Asp-Thr-Leu-Ser-Lys- Pro -Ser-Pro-Met-Pro-Val-Ser-Lys-Glu-Cys-Phe-Glu-D- Thr (SEQ ID NO:1).

In another embodiment of the present invention, the peptide has the amino acid sequence:

X-Cys-Ile-Val-Glu-Val-Ile-Ala-Asp-Ala-Leu-Ala-Lys -Pro- Ala-Pro-Met-Pro-Val-Ala-Lys-Glu-Cys-Y (SEQ ID NO:1), wherein:

X is X1 or acetyl-X1, wherein X1 is:

Lys-,

Met-Lys-,

Val-Met-Lys-,
Glu-Val-Met-Lys-,
Thr-Glu-Val-Met-Lys-,
Asp-Thr-Glu-Val-Met-Lys-,
Gly-Asp-Thr-Glu-Val-Met-Lys-,
Lys-Gly-Asp-Thr-Glu-Val-Met-Lys-,
Asn-Lys-Gly-Asp-Thr-Glu-Val-Met-Lys-,
Met-Asn-Lys-Gly-Asp-Thr-Glu-Val-Met-Lys-, or
Pro-Met-Asn-Lys-Gly-Asp-Thr-Glu-Val-Met-Lys-; and Y is -Phe-Glu or -Phe-Glu-D-Thr.

Representative peptides of the above peptide include but are not limited to the following peptides:

(a1) Lys-Cys-Ile-Val-Glu-Val-Ile-Ala-Asp-Ala-Leu-Ala-Lys -Pro-Ala-Pro-Met-Pro-Val-Ala-Lys-Glu-Cys-Phe-Glu (SEQ ID NO:1);

(a2) acetyl-Lys-Cys-Ile-Val-Glu-Val-Ile-Ala-Asp-Ala-Leu -Ala-Lys-Pro-Ala-Pro-Met-Pro-Val-Ala-Lys-Glu-Cys-Phe -Glu (SEQ ID NO:1);

(a3) Lys-Cys-Ile-Val-Glu-Val-Ile-Ala-Asp-Ala-Leu-Ala-Lys -Pro-Ala-Pro-Met-Pro-Val-Ala-Lys-Glu-Cys-Phe-Glu-D-Thr (SEQ ID NO:1);

(a4) acetyl-Lys-Cys-Ile-Val-Glu-Val-Ile-Ala-Asp-Ala-Leu -Ala-Lys-Pro-Ala-Pro-Met-Pro-Val-Ala-Lys-Glu-Cys-Phe -Glu-D-Thr (SEQ ID NO:1);

(b1) Met-Lys-Cys-Ile-Val-Glu-Val-Ile-Ala-Asp-Ala-Leu-Ala -Lys-Pro-Ala-Pro-Met-Pro-Val-Ala-Lys-Glu-Cys-Phe-Glu (SEQ ID NO:1);

(b2) acetyl-Met-Lys-Cys-Ile-Val-Glu-Val-Ile-Ala-Asp-Ala -Leu-Ala-Lys-Pro-Ala-Pro-Met-Pro-Val-Ala-Lys-Glu-Cys -Phe-Glu (SEQ ID NO:1);

(b3) Met-Lys-Cys-Ile-Val-Glu-Val-Ile-Ala-Asp-Ala-Leu-Ala -Lys-Pro-Ala-Pro-Met-Pro-Val-Ala-Lys-Glu-Cys-Phe-Glu -D-Thr (SEQ ID NO:1);

(b4) acetyl-Met-Lys-Cys-Ile-Val-Glu-Val-Ile-Ala-Asp-Ala -Leu-Ala-Lys-Pro-Ala-Pro-Met-Pro-Val-Ala-Lys-Glu-Cys -Phe-Glu-D-Thr (SEQ ID NO:1);

(c1) Val-Met-Lys-Cys-Ile-Val-Glu-Val-Ile-Ala-Asp-Ala-Leu -Ala-Lys-Pro-Ala-Pro-Met-Pro-Val-Ala-Lys-Glu-Cys-Phe -Glu (SEQ ID NO:1);

(c2) acetyl-Val-Met-Lys-Cys-Ile-Val-Glu-Val-Ile-Ala-Asp -Ala-Leu-Ala-Lys-Pro-Ala-Pro-Met-Pro-Val-Ala-Lys-Glu -Cys-Phe-Glu (SEQ ID NO:1);

(c3) Val-Met-Lys-Cys-Ile-Val-Glu-Val-Ile-Ala-Asp-Ala-Leu -Ala-Lys-Pro-Ala-Pro-Met-Pro-Val-Ala-Lys-Glu-Cys-Phe -Glu-D-Thr (SEQ ID NO:1);

(c4) acetyl-Val-Met-Lys-Cys-Ile-Val-Glu-Val-Ile-Ala-Asp -Ala-Leu-Ala-Lys-Pro-Ala-Pro-Met-Pro-Val-Ala-Lys-Glu -Cys-Phe-Glu-D-Thr (SEQ ID NO:1);

(d1) Glu-Val-Met-Lys-Cys-Ile-Val-Glu-Val-Ile-Ala-Asp-Ala -Leu-Ala-Lys-Pro-Ala-Pro-Met-Pro-Val-Ala-Lys-Glu-Cys -Phe-Glu (SEQ ID NO:1);

(d2) acetyl-Glu-Val-Met-Lys-Cys-Ile-Val-Glu-Val-Ile-Ala -Asp-Ala-Leu-Ala-Lys-Pro-Ala-Pro-Met-Pro-Val-Ala-Lys -Glu-Cys-Phe-Glu (SEQ ID NO:1);

(d3) Glu-Val-Met-Lys-Cys-Ile-Val-Glu-Val-Ile-Ala-Asp-Ala -Leu-Ala-Lys-Pro-Ala-Pro-Met-Pro-Val-Ala-Lys-Glu-Cys -Phe-Glu-D-Thr (SEQ ID NO:1);

(d4) acetyl-Glu-Val-Met-Lys-Cys-Ile-Val-Glu-Val-Ile-Ala -Asp-Ala-Leu-Ala-Lys-Pro-Ala-Pro-Met-Pro-Val-Ala-Lys -Glu-Cys-Phe-Glu-D-Thr (SEQ ID NO:1);

(e1) Thr-Glu-Val-Met-Lys-Cys-Ile-Val-Glu-Val-Ile-Ala-Asp -Ala-Leu-Ala-Lys-Pro-Ala-Pro-Met-Pro-Val-Ala-Lys-Glu -Cys-Phe-Glu (SEQ ID NO:1);

(e2) acetyl-Thr-Glu-Val-Met-Lys-Cys-Ile-Val-Glu-Val-Ile -Ala-Asp-Ala-Leu-Ala-Lys-Pro-Ala-Pro-Met-Pro-Val-Ala -Lys-Glu-Cys-Phe-Glu (SEQ ID NO:1);

(e3) Thr-Glu-Val-Met-Lys-Cys-Ile-Val-Glu-Val-Ile-Ala-Asp -Ala-Leu-Ala-Lys-Pro-Ala-Pro-Met-Pro-Val-Ala-Lys-Glu -Cys-Phe-Glu-D-Thr (SEQ ID NO:1);

(e4) acetyl-Thr-Glu-Val-Met-Lys-Cys-Ile-Val-Glu-Val-Ile -Ala-Asp-Ala-Leu-Ala-Lys-Pro-Ala-Pro-Met-Pro-Val-Ala -Lys-Glu-Cys-Phe-Glu-D-Thr (SEQ ID NO:1);

(f1) Asp-Thr-Glu-Val-Met-Lys-Cys-Ile-Val-Glu-Val-Ile-Ala -Asp-Ala-Leu-Ala-Lys-Pro-Ala-Pro-Met-Pro-Val-Ala-Lys -Glu-Cys-Phe-Glu (SEQ ID NO:1);

(f2) acetyl-Asp-Thr-Glu-Val-Met-Lys-Cys-Ile-Val-Glu-Val -Ile-Ala-Asp-Ala-Leu-Ala-Lys-Pro-Ala-Pro-Met-Pro-Val -Ala-Lys-Glu-Cys-Phe-Glu (SEQ ID NO:1);

(f3) Asp-Thr-Glu-Val-Met-Lys-Cys-Ile-Val-Glu-Val-Ile-Ala -Asp-Ala-Leu-Ala-Lys-Pro-Ala-Pro-Met-Pro-Val-Ala-Lys -Glu-Cys-Phe-Glu-D-Thr (SEQ ID NO:1);

(f4) acetyl-Asp-Thr-Glu-Val-Met-Lys-Cys-Ile-Val-Glu-Val -Ile-Ala-Asp-Ala-Leu-Ala-Lys-Pro-Ala-Pro-Met-Pro-Val -Ala-Lys-Glu-Cys-Phe-Glu-D-Thr (SEQ ID NO:1);

(g1) Gly-Asp-Thr-Glu-Val-Met-Lys-Cys-Ile-Val-Glu-Val-Ile -Ala-Asp-Ala-Leu-Ala-Lys-Pro-Ala-Pro-Met-Pro-Val-Ala -Lys-Glu-Cys-Phe-Glu (SEQ ID NO:1);

(g2) acetyl-Gly-Asp-Thr-Glu-Val-Met-Lys-Cys-Ile-Val-Glu -Val-Ile-Ala-Asp-Ala-Leu-Ala-Lys-Pro-Ala-Pro-Met-Pro -Val-Ala-Lys-Glu-Cys-Phe-Glu (SEQ ID NO:1);

(g3) Gly-Asp-Thr-Glu-Val-Met-Lys-Cys-Ile-Val-Glu-Val-Ile -Ala-Asp-Ala-Leu-Ala-Lys-Pro-Ala-Pro-Met-Pro-Val-Ala -Lys-Glu-Cys-Phe-Glu-D-Thr (SEQ ID NO:1);

(g4) acetyl-Gly-Asp-Thr-Glu-Val-Met-Lys-Cys-Ile-Val-Glu -Val-Ile-Ala-Asp-Ala-Leu-Ala-Lys-Pro-Ala-Pro-Met-Pro -Val-Ala-Lys-Glu-Cys-Phe-Glu-D-Thr (SEQ ID NO:1);

(h1) Lys-Gly-Asp-Thr-Glu-Val-Met-Lys-Cys-Ile-Val-Glu-Val -Ile-Ala-Asp-Ala-Leu-Ala-Lys-Pro-Ala-Pro-Met-Pro-Val -Ala-Lys-Glu-Cys-Phe-Glu (SEQ ID NO:1);

(h2) acetyl-Lys-Gly-Asp-Thr-Glu-Val-Met-Lys-Cys-Ile-Val -Glu-Val-Ile-Ala-Asp-Ala-Leu-Ala-Lys-Pro-Ala-Pro-Met -Pro-Val-Ala-Lys-Glu-Cys-Phe-Glu (SEQ ID NO:1);

(h3) Lys-Gly-Asp-Thr-Glu-Val-Met-Lys-Cys-Ile-Val-Glu-Val -Ile-Ala-Asp-Ala-Leu-Ala-Lys-Pro-Ala-Pro-Met-Pro-Val -Ala-Lys-Glu-Cys-Phe-Glu-D-Thr (SEQ ID NO:1);

(h4) acetyl-Lys-Gly-Asp-Thr-Glu-Val-Met-Lys-Cys-Ile-Val -Glu-Val-Ile-Ala-Asp-Ala-Leu-Ala-Lys-Pro-Ala-Pro-Met -Pro-Val-Ala-Lys-Glu-Cys-Phe-Glu-D-Thr (SEQ ID NO:1);

(i1) Asn-Lys-Gly-Asp-Thr-Glu-Val-Met-Lys-Cys-Ile-Val-Glu -Val-Ile-Ala-Asp-Ala-Leu-Ala-Lys-Pro-Ala-Pro-Met-Pro -Val-Ala-Lys-Glu-Cys-Phe-Glu (SEQ ID NO:1);

(i2) acetyl-Asn-Lys-Gly-Asp-Thr-Glu-Val-Met-Lys-Cys-Ile -Val-Glu-Val-Ile-Ala-Asp-Ala-Leu-Ala-Lys-Pro-Ala-Pro -Met-Pro-Val-Ala-Lys-Glu-Cys-Phe-Glu (SEQ ID NO:1);

(i3) Asn-Lys-Gly-Asp-Thr-Glu-Val-Met-Lys-Cys-Ile-Val-Glu -Val-Ile-Ala-Asp-Ala-Leu-Ala-Lys-Pro-Ala-Pro-Met-Pro -Val-Ala-Lys-Glu-Cys-Phe-Glu-D-Thr (SEQ ID NO:1);

(i4) acetyl-Asn-Lys-Gly-Asp-Thr-Glu-Val-Met-Lys-Cys-Ile -Val-Glu-Val-Ile-Ala-Asp-Ala-Leu-Ala-Lys-Pro-Ala-Pro -Met-Pro-Val-Ala-Lys-Glu-Cys-Phe-Glu-D-Thr (SEQ ID NO:1);

(j1) Met-Asn-Lys-Gly-Asp-Thr-Glu-Val-Met-Lys-Cys-Ile-Val -Glu-Val-Ile-Ala-Asp-Ala-Leu-Ala-Lys-Pro-Ala-Pro-Met -Pro-Val-Ala-Lys-Glu-Cys-Phe-Glu (SEQ ID NO:1);

(j2) acetyl-Met-Asn-Lys-Gly-Asp-Thr-Glu-Val-Met-Lys-Cys -Ile-Val-Glu-Val-Ile-Ala-Asp-Ala-Leu-Ala-Lys-Pro-Ala -Pro-Met-Pro-Val-Ala-Lys-Glu-Cys-Phe-Glu (SEQ ID NO:1);

(j3) Met-Asn-Lys-Gly-Asp-Thr-Glu-Val-Met-Lys-Cys-Ile-Val -Glu-Val-Ile-Ala-Asp-Ala-Leu-Ala-Lys-Pro-Ala-Pro-Met -Pro-Val-Ala-Lys-Glu-Cys-Phe-Glu-D-Thr (SEQ ID NO:1);

(j4) acetyl-Met-Asn-Lys-Gly-Asp-Thr-Glu-Val-Met-Lys-Cys -Ile-Val-Glu-Val-Ile-Ala-Asp-Ala-Leu-Ala-Lys-Pro- Ala -Pro-Met-Pro-Val-Ala-Lys-Glu-Cys-Phe-Glu-D-Thr (SEQ ID NO:1);

(k1) Pro-Met-Asn-Lys-Gly-Asp-Thr-Glu-Val-Met-Lys-Cys-Ile -Val-Glu-Val-Ile-Ala-Asp-Ala-Leu-Ala-Lys-Pro-Ala-Pro -Met-Pro-Val-Ala-Lys-Glu-Cys-Phe-Glu (SEQ ID NO:1);

(k2) acetyl-Pro-Met-Asn-Lys-Gly-Asp-Thr-Glu-Val-Met-Lys -Cys-Ile-Val-Glu-Val-Ile-Ala-Asp-Ala-Leu-Ala-Lys-Pro -Ala-Pro-Met-Pro-Val-Ala-Lys-Glu-Cys-Phe-Glu (SEQ ID NO:1);

(k3) Pro-Met-Asn-Lys-Gly-Asp-Thr-Glu-Val-Met-Lys-Cys-Ile -Val-Glu-Val-Ile-Ala-Asp-Ala-Leu-Ala-Lys-Pro-Ala-Pro -Met-Pro-Val-Ala-Lys-Glu-Cys-Phe-Glu-D-Thr (SEQ ID NO:1); and (k4) acetyl-Pro-Met-Asn-Lys-Gly-Asp-Thr-Glu-Val-Met-Lys -Cys-Ile-Val-Glu-Val-Ile-Ala-Asp-Ala-Leu-Ala-Lys-Pro -Ala-Pro-Met-Pro-Val-Ala-Lys-Glu-Cys-Phe-Glu-D-Thr (SEQ ID NO:1).

The peptides of the present invention may be synthesized using solid phase synthesis using tBoc or Fmoc protection strategies, utilizing automated instruments such as the Applied Biosystems 430A, and the like. The peptides of the present invention may be in reduced form or circularized, and are preferably circularized. The circularized form may be obtained by oxidizing the cysteine residues to form disulfide bonds by standard oxidation procedures such as air oxidation. It is also within the confines of the present invention that the cysteine residues are replaced with lanthionine residues or similar bifunctional residues which may be linked together by a pseudopeptide bond.

The present invention also provides one or more of the peptides above and a pharmaceutically acceptable carrier. The carrier must be "acceptable" in the sense of being compatible with the other ingredients of the formulation and not deleterious to the recipient thereof. The peptide may be formulated with one or more pharmaceutically acceptable diluents or carriers, and optionally, any other ingredients which may be therapeutic per se, and/or may be synergistic with the peptides of the present invention. These include chemotherapeutic agents known to inhibit parathyroid hormone secretion. The concentration of the peptide present in the formulation will depend upon the choice of carrier as well as the results desired.

For intravenous, intramuscular, subcutaneous, or intraperitoneal administration, the peptide is combined with a sterile aqueous solution which is preferably isotonic with the blood of the recipient. Such formulations may be prepared by combining the peptide with water containing physiologically compatible substances such as sodium chloride, glycine, and the like, and having a buffered pH compatible with physiological conditions to produce an aqueous solution, and rendering said solution sterile. The formulations may be present in unit or multi-dose containers such as sealed ampoules or vials.

Formulations suitable for parenteral administration conveniently comprise a sterile aqueous preparation of the peptide which is preferably made isotonic. Preparations for injections may also be formulated by suspending the peptide in non-aqueous solvent, such as vegetable oil, synthetic aliphatic acid glycerides, esters of higher aliphatic acids or propylene glycol.

The present invention further provides a method for inhibiting parathyroid hormone secretion which comprising administering to a subject a parathyroid hormone secreting amount of one or more of the peptides above. As used herein "subject" is any mammal which suffers from abnormal secretion of parathyroid hormone secretion, and is preferably human.

Since excess parathyroid hormone leads to alteration in function of cells of bone, renal tubules, and gastrointestinal mucosa, and may result in kidney stones and calcium deposits in renal tubules, generalized decalcification of bone (osteoporosis), localized bone cysts, and hypercalcemia, the present invention further provides a method for treating or preventing these complications associated with excess parathyroid secretion.

The administration may be affected by means known to those skilled in the art such as intravenous, subcutaneous, intramuscular, or intraperitoneal routes of administration. The dosage form and amount can be readily established by reference to known chemotherapeutic treatments of hyperparathyroidism, or other therapies involving similarly sized peptides. In general, however, the dosage of the peptide will be within the range of about 0.01 µg/kg to about 100 mg/kg, and preferably between about 1 µg/kg and about 10 mg/kg. The actual dose will depend upon the route of administration, the pharmacokinetic properties of the individual treated, as well as the results desired.

The present invention is described in the following Experimental Details Section which is set forth to aid in the understanding of the invention, and should not be construed to limit in any way the invention as defined in the claims which follow thereafter.

Experimental Details Section

A. Synthesis of Peptides

Peptides were synthesized by solid phase peptide synthesis using either tBoc or Fmoc protection strategies, similar to those routinely used on automated instruments such as the Applied Biosystems 430A instrument or similar to those, outlined in "Synthetic Peptides: A User's Guide", Gregory A. Grant, editor, W. H. Freeman & Co. publisher, New York (1992). After cleavage from the resin by HF (for tBoc strategy) or trifluoracetic acid (Fmoc strategy), the peptides were extracted with acetic acid solutions, lyophilized and then purified by reversed phase high performance liquid chromatography on a C-18 or C-8 bonded phase column. The disulfide bond was formed by simple air oxidation. The structures of the peptides were verified by mass spectrometry and amino acid composition analysis.

The following peptides were synthesized as described above:

Peptide I: Lys-Cys-Ile-Val-Glu-Val-Ile-Ser-Asp-Thr-Leu -Ser-Lys-Pro-Ser-Pro-Met-Pro-Val-Ser-Lys-Glu-Cys-Phe-Glu (SEQ ID NO:1);

Peptide II: acetyl-Lys-Cys-Ile-Val-Glu-Val-Ile-Ser-Asp -Thr-Leu-Ser-Lys-Pro-Ser-Pro-Met-Pro-Val-Ser-Lys-Glu-Cys -Phe-Glu-D-Thr (SEQ ID NO:1);

Peptide III: acetyl-Lys-Cys-Ile-Val-Glu-Val-Ile-Ala-Asp -Ala-Leu-Ala-Lys-Pro-Ala-Pro-Met-Pro-Val-Ala-Lys-Glu-Cys -Phe-Glu-D-Thr (SEQ ID NO:1);

Peptide IV: Asp-Thr-Glu-Val-Met-Lys-Cys-Ile-Val-Glu-Val -Ile-Ser-Asp-Thr-Leu-Ser-Lys-Pro-Ser-Pro-Met-Pro-Val-Ser -Lys-Glu-Cys-Phe-Glu (SEQ ID NO:1);

Peptide V: Pro-Met-Asn-Lys-Gly-Asp-Thr-Glu-Val-Met-Lys -Cys-Ile-Val-Glu-Val-Ile-Ser-Asp-Thr-Leu-Ser-Lys-Pro-Ser -Pro-Met-Pro-Val-Ser-Lys-Glu-Cys-Phe-Glu (SEQ ID NO:1);

Peptide VI: acetyl-Pro-Met-Asn-Lys-Gly-Asp-Thr-Glu-Val -Met-Lys-Cys-Ile-Val-Glu-Val-Ile-Ala-Asp-Ala-Leu-Ala-Lys -Pro-Ala-Pro-Met-Pro-Val-Ala-Lys-Glu-Cys-Phe-Glu-D-Thr (SEQ ID NO:1); and Peptide CGA(1–40): Leu-Pro-Val-Asn-Ser-Pro-Met-Asn-Lys -Gly-Asp-Thr-Glu-Val-Met-Lys-Cys-Ile-Val-Glu-Val-Ile-Ser -Asp-Thr-Leu-Ser-Lys-Pro-Ser-Pro-Met-Pro-Val-Ser-Lys-Glu -Cys-Phe-Glu (SEQ ID NO:2).

B. Parathyroid Cell Preparation

Parathyroid glands were obtained by neck dissection of animals from a nearby abattoir, trimmed of excess fat, and minced. Tissue fragments were enzymatically digested for 3 hours in sterile Eagle's medium) containing 2 mg/ml collagenase P, 0.75 mM magnesium, and 1 mM calcium according to the method described by Brown et al., *Endocrinology* 90:1582–1588 (1976). After digestion the cells were filtered through 200M sterile gauze, rinsed four times in sterile Eagle's medium, and plated in 24-well Falcon dishes.

C. Biological Assays

Assays were performed with freshly prepared, suspended cells as described above. For each assay 200,000 cells were used. Before incubation, cell number and viability were determined by direct cell count with a hemocytometer and trypan blue dye exclusion, respectively. 100 mM peptide was incubated with the bovine cells at 0.05 mM calcium ion concentration for one hour. Peptides I–VI were used in the assays. Calcium ion concentrations of 0.05 mM, 1.25 mM, and 2.0 mM were used as negative controls (the maximal amount of parathyroid hormone is secreted under conditions of low calcium ion concentration (0.05 mM); the minimum level is secreted under conditions of high calcium ion concentration (2.0 mM)). Peptide $CGA_{1-40}$ was used as the positive control.

Parathyroid hormone secretion released from the primary cultures of bovine parathyroid cells was quantitated by radioimmunoassay. At the beginning of each experiment, old medium was removed, and the cells were washed twice and replenished with fresh medium containing 2% fetal bovine serum, 1 mM magnesium, and the desired levels of calcium and the appropriate peptide to be tested. Each experimental condition was conducted in quadruplicate. After 1 hour of incubation the medium was removed for assay of PTH and the cells were harvested and lysed for protein determination.

The C-terminal assay for PTH employed antiserum raised against crude bovine parathyroid extract. This antiserum (GPO 13) cross-reacts equally with hPTH-(52–84) and bPTH-(1–84). Highly purified hPTH-(52–84) (Bachem, Torrence, Calif.) was used for labeling with $^{125}I$ and for assay standard. In all assays, standards and unknowns were measured in triplicate. Statistical analysis was performed and a P value less than 0.05 or better was judged significant.

C. Results

The PTH secretion from the bovine parathyroid cells as measured by radioimmunoassay for the controls and Peptides I–VI were as follows:

| Culture Additive | PTH (ng/ml) |
|---|---|
| Low Calcium (0.5 mM) | 92 ± 6.8 |
| Normal Calcium (1.25 mM) | 57 ± 4.8 |
| High Calcium (2.0 mM) | 39 ± 6.8 |
| CGA1-40 (positive control) | 47 ± 5.2 |
| Peptide I + 0.5 mM Calcium | 57 ± 1.9 |
| Peptide II + 0.5 mM Calcium | 59 ± 6.1 |
| Peptide III + 0.5 mM Calcium | 65 ± 5.2 |
| Peptide IV + 0.5 mM Calcium | 56 ± 6.5 |
| Peptide V + 0.5 mM Calcium | 49 ± 5 |
| Peptide VI + 0.5 mM Calcium | 48 ± 3.9 |

All publications mentioned hereinabove are hereby incorporated by reference in their entirety.

Although the invention herein has been described with reference to particular embodiments, it is to be understood that these embodiments are merely illustrative of various aspects of the invention. Thus, it is to be understood that numerous modifications may be made in the illustrative embodiments and other arrangements may be devised without departing from the spirit and scope of the invention in the appended claims.

---

What is claimed is:

1. A synthetic chromogranin A peptide having the amino acid sequence:
X-A-Ile-Val-Glu-Val-Ile-B-Asp-C-Leu-B-Lys-Pro-B-Pro-Met -Pro-Val-B-Lys-Glu-A-Y (SEQ ID NO:1),
wherein:
X is X1 or acetyl-X1, wherein X1 is:
Lys-,
Met-Lys-,
Val-Met-Lys-,
Glu-Val-Met-Lys-,
Thr-Glu-Val-Met-Lys-,
Asp-Thr-Glu-Val-Met-Lys-,
Gly-Asp-Thr-Glu-Val-Met-Lys-,
Lys-Gly-Asp-Thr-Glu-Val-Met-Lys-,
Asn-Lys-Gly-Asp-Thr-Glu-Val-Met-Lys-,
Met-Asn-Lys-Gly-Asp-Thr-Glu-Val-Met-Lys-, or
Pro-Met-Asn-Lys-Gly-Asp-Thr-Glu-Val-Met-Lys-, A is Cys or lanthionine;
B is Ser or Ala;
C is Thr or Ala; and
Y is -Phe-Glu or -Phe-Glu-D-Thr.

2. The peptide of claim 1 having the amino acid sequence:
X-Cys-Ile-Val-Glu-Val-Ile-Ser-Asp-Thr-Leu-Ser-Lys-Pro-Ser -Pro-Met-Pro-Val-Ser-Lys-Glu-Cys-Y (SEQ ID NO:1),
wherein:
X is X1 or acetyl-X1, wherein X1 is:
Lys-,
Met-Lys-,
Val-Met-Lys-,
Glu-Val-Met-Lys-,
Thr-Glu-Val-Met-Lys-,
Asp-Thr-Glu-Val-Met-Lys-,
Gly-Asp-Thr-Glu-Val-Met-Lys-,
Lys-Gly-Asp-Thr-Glu-Val-Met-Lys-,
Asn-Lys-Gly-Asp-Thr-Glu-Val-Met-Lys-,
Met-Asn-Lys-Gly-Asp-Thr-Glu-Val-Met-Lys-, or
Pro-Met-Asn-Lys-Gly-Asp-Thr-Glu-Val-Met-Lys-; and
Y is -Phe-Glu or -Phe-Glu-D-Thr.

3. The peptide of claim 2, selected from the group consisting of:
(a1) Lys-Cys-Ile-Val-Glu-Val-Ile-Ser-Asp-Thr-Leu-Ser-Lys -Pro-Ser-Pro-Met-Pro-Val-Ser-Lys-Glu-Cys-Phe-Glu (SEQ ID NO:1);
(a2) acetyl-Lys-Cys-Ile-Val-Glu-Val-Ile-Ser-Asp-Thr-Leu -Ser-Lys-Pro-Ser-Pro-Met-Pro-Val-Ser-Lys-Glu-Cys-Phe -Glu (SEQ ID NO:1);
(a3) Lys-Cys-Ile-Val-Glu-Val-Ile-Ser-Asp-Thr-Leu-Ser-Lys -Pro-Ser-Pro-Met-Pro-Val-Ser-Lys-Glu-Cys-Phe-Glu-D-Thr (SEQ ID NO:1);
(a4) acetyl-Lys-Cys-Ile-Val-Glu-Val-Ile-Ser-Asp-Thr-Leu -Ser-Lys-Pro-Ser-Pro-Met-Pro-Val-Ser-Lys-Glu-Cys-Phe -Glu-D-Thr (SEQ ID NO:1);
(b1) Met-Lys-Cys-Ile-Val-Glu-Val-Ile-Ser-Asp-Thr-Leu-Ser -Lys-Pro-Ser-Pro-Met-Pro-Val-Ser-Lys-Glu-Cys-Phe-Glu (SEQ ID NO:1);
(b2) acetyl-Met-Lys-Cys-Ile-Val-Glu-Val-Ile-Ser-Asp-Thr -Leu-Ser-Lys-Pro-Ser-Pro-Met-Pro-Val-Ser-Lys-Glu-Cys -Phe-Glu (SEQ ID NO:1);
(b3) Met-Lys-Cys-Ile-Val-Glu-Val-Ile-Ser-Asp-Thr-Leu-Ser -Lys-Pro-Ser-Pro-Met-Pro-Val-Ser-Lys-Glu-Cys-Phe-Glu-D -Thr (SEQ ID NO:1);
(b4) acetyl-Met-Lys-Cys-Ile-Val-Glu-Val-Ile-Ser-Asp-Thr -Leu-Ser-Lys-Pro-Ser-Pro-Met-Pro-Val-Ser-Lys-Glu-Cys -Phe-Glu-D-Thr (SEQ ID NO:1);
(c1) Val-Met-Lys-Cys-Ile-Val-Glu-Val-Ile-Ser-Asp-Thr-Leu -Ser-Lys-Pro-Ser-Pro-Met-Pro-Val-Ser-Lys-Glu-Cys-Phe -Glu (SEQ ID NO:1);
(c2) acetyl-Val-Met-Lys-Cys-Ile-Val-Glu-Val-Ile-Ser-Asp -Thr-Leu-Ser-Lys-Pro-Ser-Pro-Met-Pro-Val-Ser-Lys-Glu -Cys-Phe-Glu (SEQ ID NO:1);

(c3) Val-Met-Lys-Cys-Ile-Val-Glu-Val-Ile-Ser-Asp-Thr-Leu -Ser-Lys-Pro-Ser-Pro-Met-Pro-Val-Ser-Lys-Glu-Cys-Phe -Glu-D-Thr (SEQ ID NO:1);

(c4) acetyl-Val-Met-Lys-Cys-Ile-Val-Glu-Val-Ile-Ser-Asp -Thr-Leu-Ser-Lys-Pro-Ser-Pro-Met-Pro-Val-Ser-Lys-Glu -Cys-Phe-Glu-D-Thr (SEQ ID NO:1);

(d1) Glu-Val-Met-Lys-Cys-Ile-Val-Glu-Val-Ile-Ser-Asp-Thr -Leu-Ser-Lys-Pro-Ser-Pro-Met-Pro-Val-Ser-Lys-Glu-Cys -Phe-Glu (SEQ ID NO:1);

(d2) acetyl-Glu-Val-Met-Lys-Cys-Ile-Val-Glu-Val-Ile-Ser -Asp-Thr-Leu-Ser-Lys-Pro-Ser-Pro-Met-Pro-Val-Ser-Lys -Glu-Cys-Phe-Glu (SEQ ID NO:1);

(d3) Glu-Val-Met-Lys-Cys-Ile-Val-Glu-Val-Ile-Ser-Asp-Thr -Leu-Ser-Lys-Pro-Ser-Pro-Met-Pro-Val-Ser-Lys-Glu-Cys -Phe-Glu-D-Thr (SEQ ID NO:1);

(d4) acetyl-Glu-Val-Met-Lys-Cys-Ile-Val-Glu-Val-Ile-Ser -Asp-Thr-Leu-Ser-Lys-Pro-Ser-Pro-Met-Pro-Val-Ser-Lys -Glu-Cys-Phe-Glu-D-Thr (SEQ ID NO:1);

(e1) Thr-Glu-Val-Met-Lys-Cys-Ile-Val-Glu-Val-Ile-Ser-Asp -Thr-Leu-Ser-Lys-Pro-Ser-Pro-Met-Pro-Val-Ser-Lys-Glu -Cys-Phe-Glu (SEQ ID NO:1);

(e2) acetyl-Thr-Glu-Val-Met-Lys-Cys-Ile-Val-Glu-Val-Ile -Ser-Asp-Thr-Leu-Ser-Lys-Pro-Ser-Pro-Met-Pro-Val-Ser -Lys-Glu-Cys-Phe-Glu (SEQ ID NO:1);

(e3) Thr-Glu-Val-Met-Lys-Cys-Ile-Val-Glu-Val-Ile-Ser-Asp -Thr-Leu-Ser-Lys-Pro-Ser-Pro-Met-Pro-Val-Ser-Lys-Glu -Cys-Phe-Glu-D-Thr (SEQ ID NO:1);

(e4) acetyl-Thr-Glu-Val-Met-Lys-Cys-Ile-Val-Glu-Val-Ile -Ser-Asp-Thr-Leu-Ser-Lys-Pro-Ser-Pro-Met-Pro-Val-Ser -Lys-Glu-Cys-Phe-Glu-D-Thr (SEQ ID NO:1);

(f1) Asp-Thr-Glu-Val-Met-Lys-Cys-Ile-Val-Glu-Val-Ile-Ser -Asp-Thr-Leu-Ser-Lys-Pro-Ser-Pro-Met-Pro-Val-Ser-Lys -Glu-Cys-Phe-Glu (SEQ ID NO:1);

(f2) acetyl-Asp-Thr-Glu-Val-Met-Lys-Cys-Ile-Val-Glu-Val -Ile-Ser-Asp-Thr-Leu-Ser-Lys-Pro-Ser-Pro-Met-Pro-Val -Ser-Lys-Glu-Cys-Phe-Glu (SEQ ID NO:1);

(f3) Asp-Thr-Glu-Val-Met-Lys-Cys-Ile-Val-Glu-Val-Ile-Ser -Asp-Thr-Leu-Ser-Lys-Pro-Ser-Pro-Met-Pro-Val-Ser-Lys -Glu-Cys-Phe-Glu-D-Thr (SEQ ID NO:1);

(f4) acetyl-Asp-Thr-Glu-Val-Met-Lys-Cys-Ile-Val-Glu-Val -Ile-Ser-Asp-Thr-Leu-Ser-Lys-Pro-Ser-Pro-Met-Pro-Val -Ser-Lys-Glu-Cys-Phe-Glu-D-Thr (SEQ ID NO:1);

(g1) Gly-Asp-Thr-Glu-Val-Met-Lys-Cys-Ile-Val-Glu-Val- Ile -Ser-Asp-Thr-Leu-Ser-Lys-Pro-Ser-Pro-Met-Pro-Val- Ser -Lys-Glu-Cys-Phe-Glu (SEQ ID NO:1);

(g2) acetyl-Gly-Asp-Thr-Glu-Val-Met-Lys-Cys-Ile-Val-Glu -Val-Ile-Ser-Asp-Thr-Leu-Ser-Lys-Pro-Ser-Pro-Met-Pro -Val-Ser-Lys-Glu-Cys-Phe-Glu (SEQ ID NO:1);

(g3) Gly-Asp-Thr-Glu-Val-Met-Lys-Cys-Ile-Val-Glu-Val- Ile -Ser-Asp-Thr-Leu-Ser-Lys-Pro-Ser-Pro-Met-Pro-Val- Ser -Lys-Glu-Cys-Phe-Glu-D-Thr (SEQ ID NO:1);

(g4) acetyl-Gly-Asp-Thr-Glu-Val-Met-Lys-Cys-Ile-Val-Glu -Val-Ile-Ser-Asp-Thr-Leu-Ser-Lys-Pro-Ser-Pro-Met-Pro -Val-Ser-Lys-Glu-Cys-Phe-Glu-D-Thr (SEQ ID NO:1);

(h1) Lys-Gly-Asp-Thr-Glu-Val-Met-Lys-Cys-Ile-Val-Glu- Val -Ile-Ser-Asp-Thr-Leu-Ser-Lys-Pro-Ser-Pro-Met-Pro- Val -Ser-Lys-Glu-Cys-Phe-Glu (SEQ ID NO:1);

(h2) acetyl-Lys-Gly-Asp-Thr-Glu-Val-Met-Lys-Cys-Ile-Val -Glu-Val-Ile-Ser-Asp-Thr-Leu-Ser-Lys-Pro-Ser-Pro-Met -Pro-Val-Ser-Lys-Glu-Cys-Phe-Glu (SEQ ID NO:1);

(h3) Lys-Gly-Asp-Thr-Glu-Val-Met-Lys-Cys-Ile-Val-Glu- Val -Ile-Ser-Asp-Thr-Leu-Ser-Lys-Pro-Ser-Pro-Met-Pro- Val -Ser-Lys-Glu-Cys-Phe-Glu-D-Thr (SEQ ID NO:1);

(h4) acetyl-Lys-Gly-Asp-Thr-Glu-Val-Met-Lys-Cys-Ile-Val -Glu-Val-Ile-Ser-Asp-Thr-Leu-Ser-Lys-Pro-Ser-Pro-Met -Pro-Val-Ser-Lys-Glu-Cys-Phe-Glu-D-Thr (SEQ ID NO:1);

(i1) Asn-Lys-Gly-Asp-Thr-Glu-Val-Met-Lys-Cys-Ile-Val- Glu -Val-Ile-Ser-Asp-Thr-Leu-Ser-Lys-Pro-Ser-Pro-Met- Pro -Val-Ser-Lys-Glu-Cys-Phe-Glu (SEQ ID NO:1);

(i2) acetyl-Asn-Lys-Gly-Asp-Thr-Glu-Val-Met-Lys-Cys-Ile -Val-Glu-Val-Ile-Ser-Asp-Thr-Leu-Ser-Lys-Pro-Ser-Pro -Met-Pro-Val-Ser-Lys-Glu-Cys-Phe-Glu (SEQ ID NO:1);

(i3) Asn-Lys-Gly-Asp-Thr-Glu-Val-Met-Lys-Cys-Ile-Val- Glu -Val-Ile-Ser-Asp-Thr-Leu-Ser-Lys-Pro-Ser-Pro-Met- Pro -Val-Ser-Lys-Glu-Cys-Phe-Glu-D-Thr (SEQ ID NO:1);

(i4) acetyl-Asn-Lys-Gly-Asp-Thr-Glu-Val-Met-Lys-Cys-Ile -Val-Glu-Val-Ile-Ser-Asp-Thr-Leu-Ser-Lys-Pro-Ser-Pro -Met-Pro-Val-Ser-Lys-Glu-Cys-Phe-Glu-D-Thr (SEQ ID NO:1);

(j1) Met-Asn-Lys-Gly-Asp-Thr-Glu-Val-Met-Lys-Cys-Ile- Val -Glu-Val-Ile-Ser-Asp-Thr-Leu-Ser-Lys-Pro-Ser-Pro- Met -Pro-Val-Ser-Lys-Glu-Cys-Phe-Glu (SEQ ID NO:1);

(j2) acetyl-Met-Asn-Lys-Gly-Asp-Thr-Glu-Val-Met-Lys- Cys -Ile-Val-Glu-Val-Ile-Ser-Asp-Thr-Leu-Ser-Lys-Pro- Ser -Pro-Met-Pro-Val-Ser-Lys-Glu-Cys-Phe-Glu (SEQ ID NO: 1);

(j3) Met-Asn-Lys-Gly-Asp-Thr-Glu-Val-Met-Lys-Cys-Ile- Val -Glu-Val-Ile-Ser-Asp-Thr-Leu-Ser-Lys-Pro-Ser-Pro- Met -Pro-Val-Ser-Lys-Glu-Cys-Phe-Glu-D-Thr (SEQ ID NO:1);

(j4) acetyl-Met-Asn-Lys-Gly-Asp-Thr-Glu-Val-Met-Lys- Cys -Ile-Val-Glu-Val-Ile-Ser-Asp-Thr-Leu-Ser-Lys-Pro- Ser -Pro-Met-Pro-Val-Ser-Lys-Glu-Cys-Phe-Glu-D-Thr (SEQ ID NO:1);

(k1) Pro-Met-Asn-Lys-Gly-Asp-Thr-Glu-Val-Met-Lys-Cys- Ile -Val-Glu-Val-Ile-Ser-Asp-Thr-Leu-Ser-Lys-Pro-Ser- Pro -Met-Pro-Val-Ser-Lys-Glu-Cys-Phe-Glu (SEQ ID NO:1);

(k2) acetyl-Pro-Met-Asn-Lys-Gly-Asp-Thr-Glu-Val-Met- Lys -Cys-Ile-Val-Glu-Val-Ile-Ser-Asp-Thr-Leu-Ser-Lys- Pro -Ser-Pro-Met-Pro-Val-Ser-Lys-Glu-Cys-Phe-Glu (SEQ ID NO:1);

(k3) Pro-Met-Asn-Lys-Gly-Asp-Thr-Glu-Val-Met-Lys-Cys- Ile -Val-Glu-Val-Ile-Ser-Asp-Thr-Leu-Ser-Lys-Pro-Ser- Pro -Met-Pro-Val-Ser-Lys-Glu-Cys-Phe-Glu-D-Thr (SEQ ID NO:1);

(k4) acetyl-Pro-Met-Asn-Lys-Gly-Asp-Thr-Glu-Val-Met- Lys -Cys-Ile-Val-Glu-Val-Ile-Ser-Asp-Thr-Leu-Ser-Lys- Pro -Ser-Pro-Met-Pro-Val-Ser-Lys-Glu-Cys-Phe-Glu-D- Thr (SEQ ID NO:1).

4. The peptide of claim 1 having the amino acid sequence:
X-Cys-Ile-Val-Glu-Val-Ile-Ala-Asp-Ala-Leu-Ala-Lys-Pro- Ala -Pro-Met-Pro-Val-Ala-Lys-Glu-Cys-Y (SEQ ID NO:1), wherein:

X is X1 or acetyl-X1, wherein X1 is:

Lys-,

Met-Lys-,

Val-Met-Lys-,

Glu-Val-Met-Lys-,

Thr-Glu-Val-Met-Lys-,

Asp-Thr-Glu-Val-Met-Lys-,

Gly-Asp-Thr-Glu-Val-Met-Lys-,

Lys-Gly-Asp-Thr-Glu-Val-Met-Lys-,

Asn-Lys-Gly-Asp-Thr-Glu-Val-Met-Lys-,

Met-Asn-Lys-Gly-Asp-Thr-Glu-Val-Met-Lys-, or

Pro-Met-Asn-Lys-Gly-Asp-Thr-Glu-Val-Met-Lys-; and

Y is -Phe-Glu or -Phe-Glu-D-Thr.

5. The peptide of claim 4, selected from the group consisting of:

(a1) Lys-Cys-Ile-Val-Glu-Val-Ile-Ala-Asp-Ala-Leu-Ala- Lys -Pro-Ala-Pro-Met-Pro-Val-Ala-Lys-Glu-Cys-Phe- Glu (SEQ ID NO:1);

(a2) acetyl-Lys-Cys-Ile-Val-Glu-Val-Ile-Ala-Asp-Ala-Leu -Ala-Lys-Pro-Ala-Pro-Met-Pro-Val-Ala-Lys-Glu-Cys-Phe -Glu (SEQ ID NO:1);

(a3) Lys-Cys-Ile-Val-Glu-Val-Ile-Ala-Asp-Ala-Leu-Ala-Lys -Pro-Ala-Pro-Met-Pro-Val-Ala-Lys-Glu-Cys-Phe-Glu-D-Thr (SEQ ID NO:1);

(a4) acetyl-Lys-Cys-Ile-Val-Glu-Val-Ile-Ala-Asp-Ala-Leu -Ala-Lys-Pro-Ala-Pro-Met-Pro-Val-Ala-Lys-Glu-Cys-Phe -Glu-D-Thr (SEQ ID NO:1);

(b1) Met-Lys-Cys-Ile-Val-Glu-Val-Ile-Ala-Asp-Ala-Leu-Ala -Lys-Pro-Ala-Pro-Met-Pro-Val-Ala-Lys-Glu-Cys-Phe-Glu (SEQ ID NO:1);

(b2) acetyl-Met-Lys-Cys-Ile-Val-Glu-Val-Ile-Ala-Asp-Ala -Leu-Ala-Lys-Pro-Ala-Pro-Met-Pro-Val-Ala-Lys-Glu-Cys -Phe-Glu (SEQ ID NO:1);

(b3) Met-Lys-Cys-Ile-Val-Glu-Val-Ile-Ala-Asp-Ala-Leu-Ala -Lys-Pro-Ala-Pro-Met-Pro-Val-Ala-Lys-Glu-Cys-Phe-Glu-D -Thr (SEQ ID NO:1);

(b4) acetyl-Met-Lys-Cys-Ile-Val-Glu-Val-Ile-Ala-Asp-Ala -Leu-Ala-Lys-Pro-Ala-Pro-Met-Pro-Val-Ala-Lys-Glu-Cys -Phe-Glu-D-Thr (SEQ ID NO:1);

(c1) Val-Met-Lys-Cys-Ile-Val-Glu-Val-Ile-Ala-Asp-Ala-Leu -Ala-Lys-Pro-Ala-Pro-Met-Pro-Val-Ala-Lys-Glu-Cys-Phe -Glu (SEQ ID NO:1);

(c2) acetyl-Val-Met-Lys-Cys-Ile-Val-Glu-Val-Ile-Ala-Asp -Ala-Leu-Ala-Lys-Pro-Ala-Pro-Met-Pro-Val-Ala-Lys-Glu -Cys-Phe-Glu (SEQ ID NO:1);

(c3) Val-Met-Lys-Cys-Ile-Val-Glu-Val-Ile-Ala-Asp-Ala-Leu -Ala-Lys-Pro-Ala-Pro-Met-Pro-Val-Ala-Lys-Glu-Cys-Phe -Glu-D-Thr (SEQ ID NO:1);

(c4) acetyl-Val-Met-Lys-Cys-Ile-Val-Glu-Val-Ile-Ala-Asp -Ala-Leu-Ala-Lys-Pro-Ala-Pro-Met-Pro-Val-Ala-Lys-Glu -Cys-Phe-Glu-D-Thr (SEQ ID NO:1);

(d1) Glu-Val-Met-Lys-Cys-Ile-Val-Glu-Val-Ile-Ala-Asp-Ala -Leu-Ala-Lys-Pro-Ala-Pro-Met-Pro-Val-Ala-Lys-Glu-Cys -Phe-Glu (SEQ ID NO:1);

(d2) acetyl-Glu-Val-Met-Lys-Cys-Ile-Val-Glu-Val-Ile-Ala -Asp-Ala-Leu-Ala-Lys-Pro-Ala-Pro-Met-Pro-Val-Ala-Lys -Glu-Cys-Phe-Glu (SEQ ID NO:1);

(d3) Glu-Val-Met-Lys-Cys-Ile-Val-Glu-Val-Ile-Ala-Asp-Ala -Leu-Ala-Lys-Pro-Ala-Pro-Met-Pro-Val-Ala-Lys-Glu-Cys -Phe-Glu-D-Thr (SEQ ID NO:1);

(d4) acetyl-Glu-Val-Met-Lys-Cys-Ile-Val-Glu-Val-Ile-Ala -Asp-Ala-Leu-Ala-Lys-Pro-Ala-Pro-Met-Pro-Val-Ala-Lys -Glu-Cys-Phe-Glu-D-Thr (SEQ ID NO:1);

(e1) Thr-Glu-Val-Met-Lys-Cys-Ile-Val-Glu-Val-Ile-Ala-Asp -Ala-Leu-Ala-Lys-Pro-Ala-Pro-Met-Pro-Val-Ala-Lys-Glu -Cys-Phe-Glu (SEQ ID NO:1);

(e2) acetyl-Thr-Glu-Val-Met-Lys-Cys-Ile-Val-Glu-Val-Ile -Ala-Asp-Ala-Leu-Ala-Lys-Pro-Ala-Pro-Met-Pro-Val-Ala -Lys-Glu-Cys-Phe-Glu (SEQ ID NO:1);

(e3) Thr-Glu-Val-Met-Lys-Cys-Ile-Val-Glu-Val-Ile-Ala-Asp -Ala-Leu-Ala-Lys-Pro-Ala-Pro-Met-Pro-Val-Ala-Lys-Glu -Cys-Phe-Glu-D-Thr (SEQ ID NO:1);

(e4) acetyl-Thr-Glu-Val-Met-Lys-Cys-Ile-Val-Glu-Val-Ile -Ala-Asp-Ala-Leu-Ala-Lys-Pro-Ala-Pro-Met-Pro-Val-Ala -Lys-Glu-Cys-Phe-Glu-D-Thr (SEQ ID NO:1);

(f1) Asp-Thr-Glu-Val-Met-Lys-Cys-Ile-Val-Glu-Val-Ile-Ala -Asp-Ala-Leu-Ala-Lys-Pro-Ala-Pro-Met-Pro-Val-Ala-Lys -Glu-Cys-Phe-Glu (SEQ ID NO:1);

(f2) acetyl-Asp-Thr-Glu-Val-Met-Lys-Cys-Ile-Val-Glu-Val -Ile-Ala-Asp-Ala-Leu-Ala-Lys-Pro-Ala-Pro-Met-Pro-Val -Ala-Lys-Glu-Cys-Phe-Glu (SEQ ID NO:1);

(f3) Asp-Thr-Glu-Val-Met-Lys-Cys-Ile-Val-Glu-Val-Ile-Ala -Asp-Ala-Leu-Ala-Lys-Pro-Ala-Pro-Met-Pro-Val-Ala-Lys -Glu-Cys-Phe-Glu-D-Thr (SEQ ID NO:1);

(f4) acetyl-Asp-Thr-Glu-Val-Met-Lys-Cys-Ile-Val-Glu-Val -Ile-Ala-Asp-Ala-Leu-Ala-Lys-Pro-Ala-Pro-Met-Pro-Val -Ala-Lys-Glu-Cys-Phe-Glu-D-Thr (SEQ ID NO:1);

(g1) Gly-Asp-Thr-Glu-Val-Met-Lys-Cys-Ile-Val-Glu-Val-Ile -Ala-Asp-Ala-Leu-Ala-Lys-Pro-Ala-Pro-Met-Pro-Val-Ala -Lys-Glu-Cys-Phe-Glu (SEQ ID NO:1);

(g2) acetyl-Gly-Asp-Thr-Glu-Val-Met-Lys-Cys-Ile-Val-Glu -Val-Ile-Ala-Asp-Ala-Leu-Ala-Lys-Pro-Ala-Pro-Met-Pro -Val-Ala-Lys-Glu-Cys-Phe-Glu (SEQ ID NO:1);

(g3) Gly-Asp-Thr-Glu-Val-Met-Lys-Cys-Ile-Val-Glu-Val-Ile -Ala-Asp-Ala-Leu-Ala-Lys-Pro-Ala-Pro-Met-Pro-Val-Ala -Lys-Glu-Cys-Phe-Glu-D-Thr (SEQ ID NO:1);

(g4) acetyl-Gly-Asp-Thr-Glu-Val-Met-Lys-Cys-Ile-Val-Glu -Val-Ile-Ala-Asp-Ala-Leu-Ala-Lys-Pro-Ala-Pro-Met-Pro -Val-Ala-Lys-Glu-Cys-Phe-Glu-D-Thr (SEQ ID NO:1);

(h1) Lys-Gly-Asp-Thr-Glu-Val-Met-Lys-Cys-Ile-Val-Glu-Val -Ile-Ala-Asp-Ala-Leu-Ala-Lys-Pro-Ala-Pro-Met-Pro-Val -Ala-Lys-Glu-Cys-Phe-Glu (SEQ ID NO:1);

(h2) acetyl-Lys-Gly-Asp-Thr-Glu-Val-Met-Lys-Cys-Ile-Val -Glu-Val-Ile-Ala-Asp-Ala-Leu-Ala-Lys-Pro-Ala-Pro-Met -Pro-Val-Ala-Lys-Glu-Cys-Phe-Glu (SEQ ID NO:1);

(h3) Lys-Gly-Asp-Thr-Glu-Val-Met-Lys-Cys-Ile-Val-Glu-Val -Ile-Ala-Asp-Ala-Leu-Ala-Lys-Pro-Ala-Pro-Met-Pro-Val -Ala-Lys-Glu-Cys-Phe-Glu-D-Thr (SEQ ID NO:1);

(h4) acetyl-Lys-Gly-Asp-Thr-Glu-Val-Met-Lys-Cys-Ile-Val -Glu-Val-Ile-Ala-Asp-Ala-Leu-Ala-Lys-Pro-Ala-Pro-Met -Pro-Val-Ala-Lys-Glu-Cys-Phe-Glu-D-Thr (SEQ ID NO:1);

(i1) Asn-Lys-Gly-Asp-Thr-Glu-Val-Met-Lys-Cys-Ile-Val-Glu -Val-Ile-Ala-Asp-Ala-Leu-Ala-Lys-Pro-Ala-Pro-Met-Pro -Val-Ala-Lys-Glu-Cys-Phe-Glu (SEQ ID NO:1);

(i2) acetyl-Asn-Lys-Gly-Asp-Thr-Glu-Val-Met-Lys-Cys-Ile -Val-Glu-Val-Ile-Ala-Asp-Ala-Leu-Ala-Lys-Pro-Ala-Pro -Met-Pro-Val-Ala-Lys-Glu-Cys-Phe-Glu (SEQ ID NO:1);

(i3) Asn-Lys-Gly-Asp-Thr-Glu-Val-Met-Lys-Cys-Ile-Val-Glu -Val-Ile-Ala-Asp-Ala-Leu-Ala-Lys-Pro-Ala-Pro-Met-Pro -Val-Ala-Lys-Glu-Cys-Phe-Glu-D-Thr (SEQ ID NO:1);

(i4) acetyl-Asn-Lys-Gly-Asp-Thr-Glu-Val-Met-Lys-Cys-Ile -Val-Glu-Val-Ile-Ala-Asp-Ala-Leu-Ala-Lys-Pro-Ala-Pro -Met-Pro-Val-Ala-Lys-Glu-Cys-Phe-Glu-D-Thr (SEQ ID NO:1);

(j1) Met-Asn-Lys-Gly-Asp-Thr-Glu-Val-Met-Lys-Cys-Ile-Val -Glu-Val-Ile-Ala-Asp-Ala-Leu-Ala-Lys-Pro-Ala-Pro-Met -Pro-Val-Ala-Lys-Glu-Cys-Phe-Glu (SEQ ID NO:1);

(j2) acetyl-Met-Asn-Lys-Gly-Asp-Thr-Glu-Val-Met-Lys-Cys -Ile-Val-Glu-Val-Ile-Ala-Asp-Ala-Leu-Ala-Lys-Pro-Ala -Pro-Met-Pro-Val-Ala-Lys-Glu-Cys-Phe-Glu (SEQ ID NO: 1);

(j3) Met-Asn-Lys-Gly-Asp-Thr-Glu-Val-Met-Lys-Cys-Ile-Val -Glu-Val-Ile-Ala-Asp-Ala-Leu-Ala-Lys-Pro-Ala-Pro-Met -Pro-Val-Ala-Lys-Glu-Cys-Phe-Glu-D-Thr (SEQ ID NO:1);

(j4) acetyl-Met-Asn-Lys-Gly-Asp-Thr-Glu-Val-Met-Lys-Cys -Ile-Val-Glu-Val-Ile-Ala-Asp-Ala-Leu-Ala-Lys-Pro-Ala -Pro-Met-Pro-Val-Ala-Lys-Glu-Cys-Phe-Glu-D-Thr (SEQ ID NO:1);

(k1) Pro-Met-Asn-Lys-Gly-Asp-Thr-Glu-Val-Met-Lys-Cys-Ile -Val-Glu-Val-Ile-Ala-Asp-Ala-Leu-Ala-Lys-Pro-Ala-Pro -Met-Pro-Val-Ala-Lys-Glu-Cys-Phe-Glu (SEQ ID NO:1);

(k2) acetyl-Pro-Met-Asn-Lys-Gly-Asp-Thr-Glu-Val-Met-Lys -Cys-Ile-Val-Glu-Val-Ile-Ala-Asp-Ala-Leu-Ala-Lys-Pro -Ala-Pro-Met-Pro-Val-Ala-Lys-Glu-Cys-Phe-Glu (SEQ ID NO:1);

(k3) Pro-Met-Asn-Lys-Gly-Asp-Thr-Glu-Val-Met-Lys-Cys-Ile -Val-Glu-Val-Ile-Ala-Asp-Ala-Leu-Ala-Lys-Pro-Ala-Pro -Met-Pro-Val-Ala-Lys-Glu-Cys-Phe-Glu-D-Thr (SEQ ID NO:1); and (k4) acetyl-Pro-Met-Asn-Lys-Gly-Asp-Thr-Glu-Val-Met-Lys -Cys-Ile-Val-Glu-Val-Ile-Ala-Asp-Ala-Leu-Ala-Lys-Pro -Ala-Pro-Met-Pro-Val-Ala-Lys-Glu-Cys-Phe-Glu-D-Thr (SEQ ID NO:1).

6. A peptide composition comprising a pharmaceutically acceptable carrier and a synthetic chromogranin A peptide having the amino acid sequence:

X-A-Ile-Val-Glu-Val-Ile-B-Asp-C-Leu-B-Lys-Pro-B-Pro-Met -Pro-Val-B-Lys-Glu-A-Y (SEQ ID NO:1), wherein:

X is X1 or acetyl-X1, wherein X1 is:

Lys-,
Met-Lys-,
Val-Met-Lys-,
Glu-Val-Met-Lys-,
Thr-Glu-Val-Met-Lys-,
Asp-Thr-Glu-Val-Met-Lys-,
Gly-Asp-Thr-Glu-Val-Met-Lys-,
Lys-Gly-Asp-Thr-Glu-Val-Met-Lys-,
Asn-Lys-Gly-Asp-Thr-Glu-Val-Met-Lys-,
Met-Asn-Lys-Gly-Asp-Thr-Glu-Val-Met-Lys-, or
Pro-Met-Asn-Lys-Gly-Asp-Thr-Glu-Val-Met-Lys-;

A is Cys or lanthionine;

B is Ser or Ala;

C is Thr or Ala; and

Y is -Phe-Glu or -Phe-Glu-D-Thr.

7. The peptide composition of claim 6, wherein the peptide has the amino acid sequence:

X-Cys-Ile-Val-Glu-Val-Ile-Ser-Asp-Thr-Leu-Ser-Lys-Pro-Ser -Pro-Met-Pro-Val-Ser-Lys-Glu-Cys-Y (SEQ ID NO:1), wherein:

X is X1 or acetyl-X1, wherein X1 is:

Lys-,
Met-Lys-,
Val-Met-Lys-,
Glu-Val-Met-Lys-,
Thr-Glu-Val-Met-Lys-,
Asp-Thr-Glu-Val-Met-Lys-,
Gly-Asp-Thr-Glu-Val-Met-Lys-,
Lys-Gly-Asp-Thr-Glu-Val-Met-Lys-,
Asn-Lys-Gly-Asp-Thr-Glu-Val-Met-Lys-,
Met-Asn-Lys-Gly-Asp-Thr-Glu-Val-Met-Lys-, or
Pro-Met-Asn-Lys-Gly-Asp-Thr-Glu-Val-Met-Lys-; and Y is -Phe-Glu or -Phe-Glu-D-Thr.

8. The peptide composition of claim 7, wherein the peptide is selected from the group consisting of:

(a1) Lys-Cys-Ile-Val-Glu-Val-Ile-Ser-Asp-Thr-Leu-Ser-Lys -Pro-Ser-Pro-Met-Pro-Val-Ser-Lys-Glu-Cys-Phe-Glu (SEQ ID NO:1);

(a2) acetyl-Lys-Cys-Ile-Val-Glu-Val-Ile-Ser-Asp-Thr-Leu -Ser-Lys-Pro-Ser-Pro-Met-Pro-Val-Ser-Lys-Glu-Cys-Phe -Glu (SEQ ID NO:1);

(a3) Lys-Cys-Ile-Val-Glu-Val-Ile-Ser-Asp-Thr-Leu-Ser-Lys -Pro-Ser-Pro-Met-Pro-Val-Ser-Lys-Glu-Cys-Phe-Glu-D-Thr (SEQ ID NO:1);

(a4) acetyl-Lys-Cys-Ile-Val-Glu-Val-Ile-Ser-Asp-Thr-Leu -Ser-Lys-Pro-Ser-Pro-Met-Pro-Val-Ser-Lys-Glu-Cys-Phe -Glu-D-Thr (SEQ ID NO:1);

(b1) Met-Lys-Cys-Ile-Val-Glu-Val-Ile-Ser-Asp-Thr-Leu-Ser -Lys-Pro-Ser-Pro-Met-Pro-Val-Ser-Lys-Glu-Cys-Phe-Glu (SEQ ID NO:1);

(b2) acetyl-Met-Lys-Cys-Ile-Val-Glu-Val-Ile-Ser-Asp-Thr -Leu-Ser-Lys-Pro-Ser-Pro-Met-Pro-Val-Ser-Lys-Glu-Cys -Phe-Glu (SEQ ID NO:1);

(b3) Met-Lys-Cys-Ile-Val-Glu-Val-Ile-Ser-Asp-Thr-Leu-Ser -Lys-Pro-Ser-Pro-Met-Pro-Val-Ser-Lys-Glu-Cys-Phe-Glu-D -Thr (SEQ ID NO:1);

(b4) acetyl-Met-Lys-Cys-Ile-Val-Glu-Val-Ile-Ser-Asp-Thr -Leu-Ser-Lys-Pro-Ser-Pro-Met-Pro-Val-Ser-Lys-Glu-Cys -Phe-Glu-D-Thr (SEQ ID NO:1);

(c1) Val-Met-Lys-Cys-Ile-Val-Glu-Val-Ile-Ser-Asp-Thr-Leu -Ser-Lys-Pro-Ser-Pro-Met-Pro-Val-Ser-Lys-Glu-Cys-Phe -Glu (SEQ ID NO:1);

(c2) acetyl-Val-Met-Lys-Cys-Ile-Val-Glu-Val-Ile-Ser-Asp -Thr-Leu-Ser-Lys-Pro-Ser-Pro-Met-Pro-Val-Ser-Lys-Glu -Cys-Phe-Glu (SEQ ID NO:1);

(c3) Val-Met-Lys-Cys-Ile-Val-Glu-Val-Ile-Ser-Asp-Thr-Leu -Ser-Lys-Pro-Ser-Pro-Met-Pro-Val-Ser-Lys-Glu-Cys-Phe -Glu-D-Thr (SEQ ID NO:1);

(c4) acetyl-Val-Met-Lys-Cys-Ile-Val-Glu-Val-Ile-Ser-Asp -Thr-Leu-Ser-Lys-Pro-Ser-Pro-Met-Pro-Val-Ser-Lys-Glu -Cys-Phe-Glu-D-Thr (SEQ ID NO:1);

(d1) Glu-Val-Met-Lys-Cys-Ile-Val-Glu-Val-Ile-Ser-Asp-Thr -Leu-Ser-Lys-Pro-Ser-Pro-Met-Pro-Val-Ser-Lys-Glu-Cys -Phe-Glu (SEQ ID NO:1);

(d2) acetyl-Glu-Val-Met-Lys-Cys-Ile-Val-Glu-Val-Ile-Ser -Asp-Thr-Leu-Ser-Lys-Pro-Ser-Pro-Met-Pro-Val-Ser-Lys -Glu-Cys-Phe-Glu (SEQ ID NO:1);

(d3) Glu-Val-Met-Lys-Cys-Ile-Val-Glu-Val-Ile-Ser-Asp-Thr -Leu-Ser-Lys-Pro-Ser-Pro-Met-Pro-Val-Ser-Lys-Glu-Cys -Phe-Glu-D-Thr (SEQ ID NO:1);

(d4) acetyl-Glu-Val-Met-Lys-Cys-Ile-Val-Glu-Val-Ile-Ser -Asp-Thr-Leu-Ser-Lys-Pro-Ser-Pro-Met-Pro-Val-Ser-Lys -Glu-Cys-Phe-Glu-D-Thr (SEQ ID NO:1);

(e1) Thr-Glu-Val-Met-Lys-Cys-Ile-Val-Glu-Val-Ile-Ser-Asp -Thr-Leu-Ser-Lys-Pro-Ser-Pro-Met-Pro-Val-Ser-Lys-Glu -Cys-Phe-Glu (SEQ ID NO:1);

(e2) acetyl-Thr-Glu-Val-Met-Lys-Cys-Ile-Val-Glu-Val-Ile -Ser-Asp-Thr-Leu-Ser-Lys-Pro-Ser-Pro-Met-Pro-Val-Ser -Lys-Glu-Cys-Phe-Glu (SEQ ID NO:1);

(e3) Thr-Glu-Val-Met-Lys-Cys-Ile-Val-Glu-Val-Ile-Ser-Asp -Thr-Leu-Ser-Lys-Pro-Ser-Pro-Met-Pro-Val-Ser-Lys-Glu -Cys-Phe-Glu-D-Thr (SEQ ID NO:1);

(e4) acetyl-Thr-Glu-Val-Met-Lys-Cys-Ile-Val-Glu-Val-Ile -Ser-Asp-Thr-Leu-Ser-Lys-Pro-Ser-Pro-Met-Pro-Val-Ser -Lys-Glu-Cys-Phe-Glu-D-Thr (SEQ ID NO:1);

(f1) Asp-Thr-Glu-Val-Met-Lys-Cys-Ile-Val-Glu-Val-Ile-Ser -Asp-Thr-Leu-Ser-Lys-Pro-Ser-Pro-Met-Pro-Val-Ser-Lys -Glu-Cys-Phe-Glu (SEQ ID NO:1);

(f2) acetyl-Asp-Thr-Glu-Val-Met-Lys-Cys-Ile-Val-Glu-Val -Ile-Ser-Asp-Thr-Leu-Ser-Lys-Pro-Ser-Pro-Met-Pro-Val -Ser-Lys-Glu-Cys-Phe-Glu (SEQ ID NO:1);

(f3) Asp-Thr-Glu-Val-Met-Lys-Cys-Ile-Val-Glu-Val-Ile-Ser -Asp-Thr-Leu-Ser-Lys-Pro-Ser-Pro-Met-Pro-Val-Ser-Lys -Glu-Cys-Phe-Glu-D-Thr (SEQ ID NO:1);

(f4) acetyl-Asp-Thr-Glu-Val-Met-Lys-Cys-Ile-Val-Glu-Val -Ile-Ser-Asp-Thr-Leu-Ser-Lys-Pro-Ser-Pro-Met-Pro-Val -Ser-Lys-Glu-Cys-Phe-Glu-D-Thr (SEQ ID NO:1);

(g1) Gly-Asp-Thr-Glu-Val-Met-Lys-Cys-Ile-Val-Glu-Val-Ile -Ser-Asp-Thr-Leu-Ser-Lys-Pro-Ser-Pro-Met-Pro-Val-Ser -Lys-Glu-Cys-Phe-Glu (SEQ ID NO:1);

(g2) acetyl-Gly-Asp-Thr-Glu-Val-Met-Lys-Cys-Ile-Val-Glu -Val-Ile-Ser-Asp-Thr-Leu-Ser-Lys-Pro-Ser-Pro-Met-Pro -Val-Ser-Lys-Glu-Cys-Phe-Glu (SEQ ID NO:1);

(g3) Gly-Asp-Thr-Glu-Val-Met-Lys-Cys-Ile-Val-Glu-Val-Ile -Ser-Asp-Thr-Leu-Ser-Lys-Pro-Ser-Pro-Met-Pro-Val-Ser -Lys-Glu-Cys-Phe-Glu-D-Thr (SEQ ID NO:1);

(g4) acetyl-Gly-Asp-Thr-Glu-Val-Met-Lys-Cys-Ile-Val-Glu -Val-Ile-Ser-Asp-Thr-Leu-Ser-Lys-Pro-Ser-Pro-Met-Pro -Val-Ser-Lys-Glu-Cys-Phe-Glu-D-Thr (SEQ ID NO:1);

(h1) Lys-Gly-Asp-Thr-Glu-Val-Met-Lys-Cys-Ile-Val-Glu-Val -Ile-Ser-Asp-Thr-Leu-Ser-Lys-Pro-Ser-Pro-Met-Pro-Val -Ser-Lys-Glu-Cys-Phe-Glu (SEQ ID NO:1);

(h2) acetyl-Lys-Gly-Asp-Thr-Glu-Val-Met-Lys-Cys-Ile-Val -Glu-Val-Ile-Ser-Asp-Thr-Leu-Ser-Lys-Pro-Ser-Pro-Met -Pro-Val-Ser-Lys-Glu-Cys-Phe-Glu (SEQ ID NO:1);

(h3) Lys-Gly-Asp-Thr-Glu-Val-Met-Lys-Cys-Ile-Val-Glu-Val -Ile-Ser-Asp-Thr-Leu-Ser-Lys-Pro-Ser-Pro-Met-Pro-Val -Ser-Lys-Glu-Cys-Phe-Glu-D-Thr (SEQ ID NO:1);

(h4) acetyl-Lys-Gly-Asp-Thr-Glu-Val-Met-Lys-Cys-Ile-Val -Glu-Val-Ile-Ser-Asp-Thr-Leu-Ser-Lys-Pro-Ser-Pro-Met -Pro-Val-Ser-Lys-Glu-Cys-Phe-Glu-D-Thr (SEQ ID NO:1);

(i1) Asn-Lys-Gly-Asp-Thr-Glu-Val-Met-Lys-Cys-Ile-Val-Glu -Val-Ile-Ser-Asp-Thr-Leu-Ser-Lys-Pro-Ser-Pro-Met-Pro -Val-Ser-Lys-Glu-Cys-Phe-Glu (SEQ ID NO:1);

(i2) acetyl-Asn-Lys-Gly-Asp-Thr-Glu-Val-Met-Lys-Cys-Ile -Val-Glu-Val-Ile-Ser-Asp-Thr-Leu-Ser-Lys-Pro-Ser-Pro -Met-Pro-Val-Ser-Lys-Glu-Cys-Phe-Glu (SEQ ID NO:1);

(i3) Asn-Lys-Gly-Asp-Thr-Glu-Val-Met-Lys-Cys-Ile-Val-Glu -Val-Ile-Ser-Asp-Thr-Leu-Ser-Lys-Pro-Ser-Pro-Met-Pro -Val-Ser-Lys-Glu-Cys-Phe-Glu-D-Thr (SEQ ID NO:1);

(i4) acetyl-Asn-Lys-Gly-Asp-Thr-Glu-Val-Met-Lys-Cys-Ile -Val-Glu-Val-Ile-Ser-Asp-Thr-Leu-Ser-Lys-Pro-Ser-Pro -Met-Pro-Val-Ser-Lys-Glu-Cys-Phe-Glu-D-Thr (SEQ ID NO:1);

(j1) Met-Asn-Lys-Gly-Asp-Thr-Glu-Val-Met-Lys-Cys-Ile-Val -Glu-Val-Ile-Ser-Asp-Thr-Leu-Ser-Lys-Pro-Ser-Pro-Met -Pro-Val-Ser-Lys-Glu-Cys-Phe-Glu (SEQ ID NO:1);

(j2) acetyl-Met-Asn-Lys-Gly-Asp-Thr-Glu-Val-Met-Lys-Cys -Ile-Val-Glu-Val-Ile-Ser-Asp-Thr-Leu-Ser-Lys-Pro-Ser -Pro-Met-Pro-Val-Ser-Lys-Glu-Cys-Phe-Glu (SEQ ID NO: 1);

(j3) Met-Asn-Lys-Gly-Asp-Thr-Glu-Val-Met-Lys-Cys-Ile-Val -Glu-Val-Ile-Ser-Asp-Thr-Leu-Ser-Lys-Pro-Ser-Pro-Met -Pro-Val-Ser-Lys-Glu-Cys-Phe-Glu-D-Thr (SEQ ID NO:1);

(j4) acetyl-Met-Asn-Lys-Gly-Asp-Thr-Glu-Val-Met-Lys-Cys -Ile-Val-Glu-Val-Ile-Ser-Asp-Thr-Leu-Ser-Lys-Pro-Ser -Pro-Met-Pro-Val-Ser-Lys-Glu-Cys-Phe-Glu-D-Thr (SEQ ID NO:1);

(k1) Pro-Met-Asn-Lys-Gly-Asp-Thr-Glu-Val-Met-Lys-Cys-Ile -Val-Glu-Val-Ile-Ser-Asp-Thr-Leu-Ser-Lys-Pro-Ser-Pro -Met-Pro-Val-Ser-Lys-Glu-Cys-Phe-Glu (SEQ ID NO:1);

(k2) acetyl-Pro-Met-Asn-Lys-Gly-Asp-Thr-Glu-Val-Met-Lys -Cys-Ile-Val-Glu-Val-Ile-Ser-Asp-Thr-Leu-Ser-Lys-Pro -Ser-Pro-Met-Pro-Val-Ser-Lys-Glu-Cys-Phe-Glu (SEQ ID NO:1);

(k3) Pro-Met-Asn-Lys-Gly-Asp-Thr-Glu-Val-Met-Lys-Cys-Ile -Val-Glu-Val-Ile-Ser-Asp-Thr-Leu-Ser-Lys-Pro-Ser-Pro -Met-Pro-Val-Ser-Lys-Glu-Cys-Phe-Glu-D-Thr (SEQ ID NO:1);

(k4) acetyl-Pro-Met-Asn-Lys-Gly-Asp-Thr-Glu-Val-Met-Lys -Cys-Ile-Val-Glu-Val-Ile-Ser-Asp-Thr-Leu-Ser-Lys-Pro -Ser-Pro-Met-Pro-Val-Ser-Lys-Glu-Cys-Phe-Glu-D-Thr (SEQ ID NO:1).

9. The peptide composition of claim 1, wherein the peptide has the amino acid sequence:

X-Cys-Ile-Val-Glu-Val-Ile-Ala-Asp-Ala-Leu-Ala-Lys-Pro-Ala -Pro-Met-Pro-Ala-Lys-Glu-Cys-Y (SEQ ID NO:1), wherein:

X is X1 or acetyl-X1, wherein X1 is:

Lys-,
Met-Lys-,
Val-Met-Lys-,
Glu-Val-Met-Lys-,
Thr-Glu-Val-Met-Lys-,
Asp-Thr-Glu-Val-Met-Lys-,
Gly-Asp-Thr-Glu-Val-Met-Lys-,
Lys-Gly-Asp-Thr-Glu-Val-Met-Lys-,
Asn-Lys-Gly-Asp-Thr-Glu-Val-Met-Lys-,
Met-Asn-Lys-Gly-Asp-Thr-Glu-Val-Met-Lys-, or
Pro-Met-Asn-Lys-Gly-Asp-Thr-Glu-Val-Met-Lys-; and Y is -Phe-Glu or -Phe-Glu-D-Thr.

10. The peptide composition of claim 9, wherein the peptide is selected from the group consisting of:

(a1) Lys-Cys-Ile-Val-Glu-Val-Ile-Ala-Asp-Ala-Leu-Ala-Lys -Pro-Ala-Pro-Met-Pro-Val-Ala-Lys-Glu-Cys-Phe-Glu (SEQ ID NO:1);

(a2) acetyl-Lys-Cys-Ile-Val-Glu-Val-Ile-Ala-Asp-Ala-Leu -Ala-Lys-Pro-Ala-Pro-Met-Pro-Val-Ala-Lys-Glu-Cys-Phe -Glu (SEQ ID NO:1);

(a3) Lys-Cys-Ile-Val-Glu-Val-Ile-Ala-Asp-Ala-Leu-Ala-Lys -Pro-Ala-Pro-Met-Pro-Val-Ala-Lys-Glu-Cys-Phe-Glu-D-Thr (SEQ ID NO:1);

(a4) acetyl-Lys-Cys-Ile-Val-Glu-Val-Ile-Ala-Asp-Ala-Leu -Ala-Lys-Pro-Ala-Pro-Met-Pro-Val-Ala-Lys-Glu-Cys-Phe -Glu-D-Thr (SEQ ID NO:1);

(b1) Met-Lys-Cys-Ile-Val-Glu-Val-Ile-Ala-Asp-Ala-Leu-Ala -Lys-Pro-Ala-Pro-Met-Pro-Val-Ala-Lys-Glu-Cys-Phe-Glu (SEQ ID NO:1);

(b2) acetyl-Met-Lys-Cys-Ile-Val-Glu-Val-Ile-Ala-Asp-Ala -Leu-Ala-Lys-Pro-Ala-Pro-Met-Pro-Val-Ala-Lys-Glu-Cys -Phe-Glu (SEQ ID NO:1);

(b3) Met-Lys-Cys-Ile-Val-Glu-Val-Ile-Ala-Asp-Ala-Leu-Ala -Lys-Pro-Ala-Pro-Met-Pro-Val-Ala-Lys-Glu-Cys-Phe-Glu-D -Thr (SEQ ID NO:1);

(b4) acetyl-Met-Lys-Cys-Ile-Val-Glu-Val-Ile-Ala-Asp-Ala -Leu-Ala-Lys-Pro-Ala-Pro-Met-Pro-Val-Ala-Lys-Glu-Cys -Phe-Glu-D-Thr (SEQ ID NO:1);

(c1) Val-Met-Lys-Cys-Ile-Val-Glu-Val-Ile-Ala-Asp-Ala-Leu -Ala-Lys-Pro-Ala-Pro-Met-Pro-Val-Ala-Lys-Glu-Cys-Phe -Glu (SEQ ID NO:1);

(c2) acetyl-Val-Met-Lys-Cys-Ile-Val-Glu-Val-Ile-Ala-Asp -Ala-Leu-Ala-Lys-Pro-Ala-Pro-Met-Pro-Val-Ala-Lys-Glu -Cys-Phe-Glu (SEQ ID NO:1);

(c3) Val-Met-Lys-Cys-Ile-Val-Glu-Val-Ile-Ala-Asp-Ala-Leu -Ala-Lys-Pro-Ala-Pro-Met-Pro-Val-Ala-Lys-Glu-Cys-Phe -Glu-D-Thr (SEQ ID NO:1);

(c4) acetyl-Val-Met-Lys-Cys-Ile-Val-Glu-Val-Ile-Ala-Asp -Ala-Leu-Ala-Lys-Pro-Ala-Pro-Met-Pro-Val-Ala-Lys-Glu -Cys-Phe-Glu-D-Thr (SEQ ID NO:1);

(d1) Glu-Val-Met-Lys-Cys-Ile-Val-Glu-Val-Ile-Ala-Asp-Ala -Leu-Ala-Lys-Pro-Ala-Pro-Met-Pro-Val-Ala-Lys-Glu-Cys -Phe-Glu (SEQ ID NO:1);

(d2) acetyl-Glu-Val-Met-Lys-Cys-Ile-Val-Glu-Val-Ile-Ala -Asp-Ala-Leu-Ala-Lys-Pro-Ala-Pro-Met-Pro-Val-Ala-Lys -Glu-Cys-Phe-Glu (SEQ ID NO:1);

(d3) Glu-Val-Met-Lys-Cys-Ile-Val-Glu-Val-Ile-Ala-Asp-Ala -Leu-Ala-Lys-Pro-Ala-Pro-Met-Pro-Val-Ala-Lys-Glu-Cys -Phe-Glu-D-Thr (SEQ ID NO:1);

(d4) acetyl-Glu-Val-Met-Lys-Cys-Ile-Val-Glu-Val-Ile-Ala -Asp-Ala-Leu-Ala-Lys-Pro-Ala-Pro-Met-Pro-Val-Ala-Lys -Glu-Cys-Phe-Glu-D-Thr (SEQ ID NO:1);

(e1) Thr-Glu-Val-Met-Lys-Cys-Ile-Val-Glu-Val-Ile-Ala-Asp -Ala-Leu-Ala-Lys-Pro-Ala-Pro-Met-Pro-Val-Ala-Lys-Glu -Cys-Phe-Glu (SEQ ID NO:1);

(e2) acetyl-Thr-Glu-Val-Met-Lys-Cys-Ile-Val-Glu-Val-Ile -Ala-Asp-Ala-Leu-Ala-Lys-Pro-Ala-Pro-Met-Pro-Val-Ala -Lys-Glu-Cys-Phe-Glu (SEQ ID NO:1);

(e3) Thr-Glu-Val-Met-Lys-Cys-Ile-Val-Glu-Val-Ile-Ala-Asp -Ala-Leu-Ala-Lys-Pro-Ala-Pro-Met-Pro-Val-Ala-Lys-Glu -Cys-Phe-Glu-D-Thr (SEQ ID NO:1);

(e4) acetyl-Thr-Glu-Val-Met-Lys-Cys-Ile-Val-Glu-Val-Ile -Ala-Asp-Ala-Leu-Ala-Lys-Pro-Ala-Pro-Met-Pro-Val-Ala -Lys-Glu-Cys-Phe-Glu-D-Thr (SEQ ID NO:1);

(f1) Asp-Thr-Glu-Val-Met-Lys-Cys-Ile-Val-Glu-Val-Ile-Ala -Asp-Ala-Leu-Ala-Lys-Pro-Ala-Pro-Met-Pro-Val-Ala-Lys -Glu-Cys-Phe-Glu (SEQ ID NO:1);

(f2) acetyl-Asp-Thr-Glu-Val-Met-Lys-Cys-Ile-Val-Glu-Val-Ile-Ala-Asp-Ala-Leu-Ala-Lys-Pro-Ala-Pro-Met-Pro-Val-Ala-Lys-Glu-Cys-Phe-Glu (SEQ ID NO:1);

(f3) Asp-Thr-Glu-Val-Met-Lys-Cys-Ile-Val-Glu-Val-Ile-Ala-Asp-Ala-Leu-Ala-Lys-Pro-Ala-Pro-Met-Pro-Val-Ala-Lys-Glu-Cys-Phe-Glu-D-Thr (SEQ ID NO:1);

(f4) acetyl-Asp-Thr-Glu-Val-Met-Lys-Cys-Ile-Val-Glu-Val-Ile-Ala-Asp-Ala-Leu-Ala-Lys-Pro-Ala-Pro-Met-Pro-Val-Ala-Lys-Glu-Cys-Phe-Glu-D-Thr (SEQ ID NO:1);

(g1) Gly-Asp-Thr-Glu-Val-Met-Lys-Cys-Ile-Val-Glu-Val-Ile-Ala-Asp-Ala-Leu-Ala-Lys-Pro-Ala-Pro-Met-Pro-Val-Ala-Lys-Glu-Cys-Phe-Glu (SEQ ID NO:1);

(g2) acetyl-Gly-Asp-Thr-Glu-Val-Met-Lys-Cys-Ile-Val-Glu-Val-Ile-Ala-Asp-Ala-Leu-Ala-Lys-Pro-Ala-Pro-Met-Pro-Val-Ala-Lys-Glu-Cys-Phe-Glu (SEQ ID NO:1);

(g3) Gly-Asp-Thr-Glu-Val-Met-Lys-Cys-Ile-Val-Glu-Val-Ile-Ala-Asp-Ala-Leu-Ala-Lys-Pro-Ala-Pro-Met-Pro-Val-Ala-Lys-Glu-Cys-Phe-Glu-D-Thr (SEQ ID NO:1);

(g4) acetyl-Gly-Asp-Thr-Glu-Val-Met-Lys-Cys-Ile-Val-Glu-Val-Ile-Ala-Asp-Ala-Leu-Ala-Lys-Pro-Ala-Pro-Met-Pro-Val-Ala-Lys-Glu-Cys-Phe-Glu-D-Thr (SEQ ID NO:1);

(h1) Lys-Gly-Asp-Thr-Glu-Val-Met-Lys-Cys-Ile-Val-Glu-Val-Ile-Ala-Asp-Ala-Leu-Ala-Lys-Pro-Ala-Pro-Met-Pro-Val-Ala-Lys-Glu-Cys-Phe-Glu (SEQ ID NO:1);

(h2) acetyl-Lys-Gly-Asp-Thr-Glu-Val-Met-Lys-Cys-Ile-Val-Glu-Val-Ile-Ala-Asp-Ala-Leu-Ala-Lys-Pro-Ala-Pro-Met-Pro-Val-Ala-Lys-Glu-Cys-Phe-Glu (SEQ ID NO:1);

(h3) Lys-Gly-Asp-Thr-Glu-Val-Met-Lys-Cys-Ile-Val-Glu-Val-Ile-Ala-Asp-Ala-Leu-Ala-Lys-Pro-Ala-Pro-Met-Pro-Val-Ala-Lys-Glu-Cys-Phe-Glu-D-Thr (SEQ ID NO:1);

(h4) acetyl-Lys-Gly-Asp-Thr-Glu-Val-Met-Lys-Cys-Ile-Val-Glu-Val-Ile-Ala-Asp-Ala-Leu-Ala-Lys-Pro-Ala-Pro-Met-Pro-Val-Ala-Lys-Glu-Cys-Phe-Glu-D-Thr (SEQ ID NO:1);

(i1) Asn-Lys-Gly-Asp-Thr-Glu-Val-Met-Lys-Cys-Ile-Val-Glu-Val-Ile-Ala-Asp-Ala-Leu-Ala-Lys-Pro-Ala-Pro-Met-Pro-Val-Ala-Lys-Glu-Cys-Phe-Glu (SEQ ID NO:1);

(i2) acetyl-Asn-Lys-Gly-Asp-Thr-Glu-Val-Met-Lys-Cys-Ile-Val-Glu-Val-Ile-Ala-Asp-Ala-Leu-Ala-Lys-Pro-Ala-Pro-Met-Pro-Val-Ala-Lys-Glu-Cys-Phe-Glu (SEQ ID NO:1);

(i3) Asn-Lys-Gly-Asp-Thr-Glu-Val-Met-Lys-Cys-Ile-Val-Glu-Val-Ile-Ala-Asp-Ala-Leu-Ala-Lys-Pro-Ala-Pro-Met-Pro-Val-Ala-Lys-Glu-Cys-Phe-Glu-D-Thr (SEQ ID NO:1);

(i4) acetyl-Asn-Lys-Gly-Asp-Thr-Glu-Val-Met-Lys-Cys-Ile-Val-Glu-Val-Ile-Ala-Asp-Ala-Leu-Ala-Lys-Pro-Ala-Pro-Met-Pro-Val-Ala-Lys-Glu-Cys-Phe-Glu-D-Thr (SEQ ID NO:1);

(j1) Met-Asn-Lys-Gly-Asp-Thr-Glu-Val-Met-Lys-Cys-Ile-Val-Glu-Val-Ile-Ala-Asp-Ala-Leu-Ala-Lys-Pro-Ala-Pro-Met-Pro-Val-Ala-Lys-Glu-Cys-Phe-Glu (SEQ ID NO:1);

(j2) acetyl-Met-Asn-Lys-Gly-Asp-Thr-Glu-Val-Met-Lys-Cys-Ile-Val-Glu-Val-Ile-Ala-Asp-Ala-Leu-Ala-Lys-Pro-Ala-Pro-Met-Pro-Val-Ala-Lys-Glu-Cys-Phe-Glu (SEQ ID NO:1);

(j3) Met-Asn-Lys-Gly-Asp-Thr-Glu-Val-Met-Lys-Cys-Ile-Val-Glu-Val-Ile-Ala-Asp-Ala-Leu-Ala-Lys-Pro-Ala-Pro-Met-Pro-Val-Ala-Lys-Glu-Cys-Phe-Glu-D-Thr (SEQ ID NO:1);

(j4) acetyl-Met-Asn-Lys-Gly-Asp-Thr-Glu-Val-Met-Lys-Cys-Ile-Val-Glu-Val-Ile-Ala-Asp-Ala-Leu-Ala-Lys-Pro-Ala-Pro-Met-Pro-Val-Ala-Lys-Glu-Cys-Phe-Glu-D-Thr (SEQ ID NO:1);

(k1) Pro-Met-Asn-Lys-Gly-Asp-Thr-Glu-Val-Met-Lys-Cys-Ile-Val-Glu-Val-Ile-Ala-Asp-Ala-Leu-Ala-Lys-Pro-Ala-Pro-Met-Pro-Val-Ala-Lys-Glu-Cys-Phe-Glu (SEQ ID NO:1);

(k2) acetyl-Pro-Met-Asn-Lys-Gly-Asp-Thr-Glu-Val-Met-Lys-Cys-Ile-Val-Glu-Val-Ile-Ala-Asp-Ala-Leu-Ala-Lys-Pro-Ala-Pro-Met-Pro-Val-Ala-Lys-Glu-Cys-Phe-Glu (SEQ ID NO:1);

(k3) Pro-Met-Asn-Lys-Gly-Asp-Thr-Glu-Val-Met-Lys-Cys-Ile-Val-Glu-Val-Ile-Ala-Asp-Ala-Leu-Ala-Lys-Pro-Ala-Pro-Met-Pro-Val-Ala-Lys-Glu-Cys-Phe-Glu-D-Thr (SEQ ID NO:1); and (k4) acetyl-Pro-Met-Asn-Lys-Gly-Asp-Thr-Glu-Val-Met-Lys-Cys-Ile-Val-Glu-Val-Ile-Ala-Asp-Ala-Leu-Ala-Lys-Pro-Ala-Pro-Met-Pro-Val-Ala-Lys-Glu-Cys-Phe-Glu-D-Thr (SEQ ID NO:1).

11. A method for inhibiting parathyroid hormone secretion in a subject in need of such inhibition comprising administering to the subject a parathyroid hormone secretion inhibiting amount of a synthetic chromogranin A peptide having the amino acid sequence:

X-A-Ile-Val-Glu-Val-Ile-B-Asp-C-Leu-B-Lys-Pro-B-Pro-Met-Pro-Val-B-Lys-Glu-A-Y (SEQ ID NO:1), wherein:

X is X1 or acetyl-X1, wherein X1 is:
Lys-,
Met-Lys-,
Val-Met-Lys-,
Glu-Val-Met-Lys-,
Thr-Glu-Val-Met-Lys-,
Asp-Thr-Glu-Val-Met-Lys-,
Gly-Asp-Thr-Glu-Val-Met-Lys-,
Lys-Gly-Asp-Thr-Glu-Val-Met-Lys-,
Asn-Lys-Gly-Asp-Thr-Glu-Val-Met-Lys-,
Met-Asn-Lys-Gly-Asp-Thr-Glu-Val-Met-Lys-, or
Pro-Met-Asn-Lys-Gly-Asp-Thr-Glu-Val-Met-Lys-;

A is Cys or lanthionine;

B is Ser or Ala;

C is Thr or Ala; and

Y is -Phe-Glu or -Phe-Glu-D-Thr.

12. The method of claim 11, wherein the peptide has the amino acid sequence:

X-Cys-Ile-Val-Glu-Val-Ile-Ser-Asp-Thr-Leu-Ser-Lys-Pro-Ser-Pro-Met-Pro-Val-Ser-Lys-Glu-Cys-Y (SEQ ID NO:1), wherein:

X is X1 or acetyl-X1, wherein X1 is:
Lys-,
Met-Lys-,
Val-Met-Lys-,
Glu-Val-Met-Lys-,
Thr-Glu-Val-Met-Lys-,
Asp-Thr-Glu-Val-Met-Lys-,
Gly-Asp-Thr-Glu-Val-Met-Lys-,
Lys-Gly-Asp-Thr-Glu-Val-Met-Lys-,
Asn-Lys-Gly-Asp-Thr-Glu-Val-Met-Lys-,
Met-Asn-Lys-Gly-Asp-Thr-Glu-Val-Met-Lys-, or
Pro-Met-Asn-Lys-Gly-Asp-Thr-Glu-Val-Met-Lys-; and Y is -Phe-Glu or -Phe-Glu-D-Thr.

13. The method of claim 12, wherein the peptide is selected from the group consisting of:

(a1) Lys-Cys-Ile-Val-Glu-Val-Ile-Ser-Asp-Thr-Leu-Ser-Lys-Pro-Ser-Pro-Met-Pro-Val-Ser-Lys-Glu-Cys-Phe-Glu (SEQ ID NO:1);

(a2) acetyl-Lys-Cys-Ile-Val-Glu-Val-Ile-Ser-Asp-Thr-Leu-Ser-Lys-Pro-Ser-Pro-Met-Pro-Val-Ser-Lys-Glu-Cys-Phe-Glu (SEQ ID NO:1);

(a3) Lys-Cys-Ile-Val-Glu-Val-Ile-Ser-Asp-Thr-Leu-Ser-Lys-Pro-Ser-Pro-Met-Pro-Val-Ser-Lys-Glu-Cys-Phe-Glu-D-Thr (SEQ ID NO:1);

(a4) acetyl-Lys-Cys-Ile-Val-Glu-Val-Ile-Ser-Asp-Thr-Leu -Ser-Lys-Pro-Ser-Pro-Met-Pro-Val-Ser-Lys-Glu-Cys-Phe -Glu-D-Thr (SEQ ID NO:1);

(b1) Met-Lys-Cys-Ile-Val-Glu-Val-Ile-Ser-Asp-Thr-Leu-Ser -Lys-Pro-Ser-Pro-Met-Pro-Val-Ser-Lys-Glu-Cys-Phe-Glu (SEQ ID NO:1);

(b2) acetyl-Met-Lys-Cys-Ile-Val-Glu-Val-Ile-Ser-Asp-Thr -Leu-Ser-Lys-Pro-Ser-Pro-Met-Pro-Val-Ser-Lys-Glu-Cys -Phe-Glu (SEQ ID NO:1);

(b3) Met-Lys-Cys-Ile-Val-Glu-Val-Ile-Ser-Asp-Thr-Leu-Ser -Lys-Pro-Ser-Pro-Met-Pro-Val-Ser-Lys-Glu-Cys-Phe-Glu-D -Thr (SEQ ID NO:1);

(b4) acetyl-Met-Lys-Cys-Ile-Val-Glu-Val-Ile-Ser-Asp-Thr -Leu-Ser-Lys-Pro-Ser-Pro-Met-Pro-Val-Ser-Lys-Glu-Cys -Phe-Glu-D-Thr (SEQ ID NO:1);

(c1) Val-Met-Lys-Cys-Ile-Val-Glu-Val-Ile-Ser-Asp-Thr-Leu -Ser-Lys-Pro-Ser-Pro-Met-Pro-Val-Ser-Lys-Glu-Cys-Phe -Glu (SEQ ID NO:1);

(c2) acetyl-Val-Met-Lys-Cys-Ile-Val-Glu-Val-Ile-Ser-Asp -Thr-Leu-Ser-Lys-Pro-Ser-Pro-Met-Pro-Val-Ser-Lys-Glu -Cys-Phe-Glu (SEQ ID NO:1);

(c3) Val-Met-Lys-Cys-Ile-Val-Glu-Val-Ile-Ser-Asp-Thr-Leu -Ser-Lys-Pro-Ser-Pro-Met-Pro-Val-Ser-Lys-Glu-Cys-Phe -Glu-D-Thr (SEQ ID NO:1);

(c4) acetyl-Val-Met-Lys-Cys-Ile-Val-Glu-Val-Ile-Ser-Asp -Thr-Leu-Ser-Lys-Pro-Ser-Pro-Met-Pro-Val-Ser-Lys-Glu -Cys-Phe-Glu-D-Thr (SEQ ID NO:1);

(d1) Glu-Val-Met-Lys-Cys-Ile-Val-Glu-Val-Ile-Ser-Asp-Thr -Leu-Ser-Lys-Pro-Ser-Pro-Met-Pro-Val-Ser-Lys-Glu-Cys -Phe-Glu (SEQ ID NO:1);

(d2) acetyl-Glu-Val-Met-Lys-Cys-Ile-Val-Glu-Val-Ile-Ser -Asp-Thr-Leu-Ser-Lys-Pro-Ser-Pro-Met-Pro-Val-Ser-Lys -Glu-Cys-Phe-Glu (SEQ ID NO:1);

(d3) Glu-Val-Met-Lys-Cys-Ile-Val-Glu-Val-Ile-Ser-Asp-Thr -Leu-Ser-Lys-Pro-Ser-Pro-Met-Pro-Val-Ser-Lys-Glu-Cys -Phe-Glu-D-Thr (SEQ ID NO:1);

(d4) acetyl-Glu-Val-Met-Lys-Cys-Ile-Val-Glu-Val-Ile-Ser -Asp-Thr-Leu-Ser-Lys-Pro-Ser-Pro-Met-Pro-Val-Ser-Lys -Glu-Cys-Phe-Glu-D-Thr (SEQ ID NO:1);

(e1) Thr-Glu-Val-Met-Lys-Cys-Ile-Val-Glu-Val-Ile-Ser-Asp -Thr-Leu-Ser-Lys-Pro-Ser-Pro-Met-Pro-Val-Ser-Lys-Glu -Cys-Phe-Glu (SEQ ID NO:1);

(e2) acetyl-Thr-Glu-Val-Met-Lys-Cys-Ile-Val-Glu-Val-Ile -Ser-Asp-Thr-Leu-Ser-Lys-Pro-Ser-Pro-Met-Pro-Val-Ser -Lys-Glu-Cys-Phe-Glu (SEQ ID NO:1);

(e3) Thr-Glu-Val-Met-Lys-Cys-Ile-Val-Glu-Val-Ile-Ser-Asp -Thr-Leu-Ser-Lys-Pro-Ser-Pro-Met-Pro-Val-Ser-Lys-Glu -Cys-Phe-Glu-D-Thr (SEQ ID NO:1);

(e4) acetyl-Thr-Glu-Val-Met-Lys-Cys-Ile-Val-Glu-Val-Ile -Ser-Asp-Thr-Leu-Ser-Lys-Pro-Ser-Pro-Met-Pro-Val-Ser -Lys-Glu-Cys-Phe-Glu-D-Thr (SEQ ID NO:1);

(f1) Asp-Thr-Glu-Val-Met-Lys-Cys-Ile-Val-Glu-Val-Ile-Ser -Asp-Thr-Leu-Ser-Lys-Pro-Ser-Pro-Met-Pro-Val-Ser-Lys -Glu-Cys-Phe-Glu (SEQ ID NO:1);

(f2) acetyl-Asp-Thr-Glu-Val-Met-Lys-Cys-Ile-Val-Glu-Val -Ile-Ser-Asp-Thr-Leu-Ser-Lys-Pro-Ser-Pro-Met-Pro-Val -Ser-Lys-Glu-Cys-Phe-Glu (SEQ ID NO:1);

(f3) Asp-Thr-Glu-Val-Met-Lys-Cys-Ile-Val-Glu-Val-Ile-Ser -Asp-Thr-Leu-Ser-Lys-Pro-Ser-Pro-Met-Pro-Val-Ser-Lys -Glu-Cys-Phe-Glu-D-Thr (SEQ ID NO:1);

(f4) acetyl-Asp-Thr-Glu-Val-Met-Lys-Cys-Ile-Val-Glu-Val -Ile-Ser-Asp-Thr-Leu-Ser-Lys-Pro-Ser-Pro-Met-Pro-Val -Ser-Lys-Glu-Cys-Phe-Glu-D-Thr (SEQ ID NO:1);

(g1) Gly-Asp-Thr-Glu-Val-Met-Lys-Cys-Ile-Val-Glu-Val-Ile -Ser-Asp-Thr-Leu-Ser-Lys-Pro-Ser-Pro-Met-Pro-Val-Ser -Lys-Glu-Cys-Phe-Glu (SEQ ID NO:1);

(g2) acetyl-Gly-Asp-Thr-Glu-Val-Met-Lys-Cys-Ile-Val-Glu -Val-Ile-Ser-Asp-Thr-Leu-Ser-Lys-Pro-Ser-Pro-Met-Pro -Val-Ser-Lys-Glu-Cys-Phe-Glu (SEQ ID NO:1);

(g3) Gly-Asp-Thr-Glu-Val-Met-Lys-Cys-Ile-Val-Glu-Val-Ile -Ser-Asp-Thr-Leu-Ser-Lys-Pro-Ser-Pro-Met-Pro-Val-Ser -Lys-Glu-Cys-Phe-Glu-D-Thr (SEQ ID NO:1);

(g4) acetyl-Gly-Asp-Thr-Glu-Val-Met-Lys-Cys-Ile-Val-Glu -Val-Ile-Ser-Asp-Thr-Leu-Ser-Lys-Pro-Ser-Pro-Met-Pro -Val-Ser-Lys-Glu-Cys-Phe-Glu-D-Thr (SEQ ID NO:1);

(h1) Lys-Gly-Asp-Thr-Glu-Val-Met-Lys-Cys-Ile-Val-Glu-Val -Ile-Ser-Asp-Thr-Leu-Ser-Lys-Pro-Ser-Pro-Met-Pro-Val -Ser-Lys-Glu-Cys-Phe-Glu (SEQ ID NO:1);

(h2) acetyl-Lys-Gly-Asp-Thr-Glu-Val-Met-Lys-Cys-Ile-Val -Glu-Val-Ile-Ser-Asp-Thr-Leu-Ser-Lys-Pro-Ser-Pro-Met -Pro-Val-Ser-Lys-Glu-Cys-Phe-Glu (SEQ ID NO:1);

(h3) Lys-Gly-Asp-Thr-Glu-Val-Met-Lys-Cys-Ile-Val-Glu-Val -Ile-Ser-Asp-Thr-Leu-Ser-Lys-Pro-Ser-Pro-Met-Pro-Val -Ser-Lys-Glu-Cys-Phe-Glu-D-Thr (SEQ ID NO:1);

(h4) acetyl-Lys-Gly-Asp-Thr-Glu-Val-Met-Lys-Cys-Ile-Val -Glu-Val-Ile-Ser-Asp-Thr-Leu-Ser-Lys-Pro-Ser-Pro-Met -Pro-Val-Ser-Lys-Glu-Cys-Phe-Glu-D-Thr (SEQ ID NO:1);

(i1) Asn-Lys-Gly-Asp-Thr-Glu-Val-Met-Lys-Cys-Ile-Val-Glu -Val-Ile-Ser-Asp-Thr-Leu-Ser-Lys-Pro-Ser-Pro-Met-Pro -Val-Ser-Lys-Glu-Cys-Phe-Glu (SEQ ID NO:1);

(i2) acetyl-Asn-Lys-Gly-Asp-Thr-Glu-Val-Met-Lys-Cys-Ile -Val-Glu-Val-Ile-Ser-Asp-Thr-Leu-Ser-Lys-Pro-Ser-Pro -Met-Pro-Val-Ser-Lys-Glu-Cys-Phe-Glu (SEQ ID NO:1);

(i3) Asn-Lys-Gly-Asp-Thr-Glu-Val-Met-Lys-Cys-Ile-Val-Glu -Val-Ile-Ser-Asp-Thr-Leu-Ser-Lys-Pro-Ser-Pro-Met-Pro -Val-Ser-Lys-Glu-Cys-Phe-Glu-D-Thr (SEQ ID NO:1);

(i4) acetyl-Asn-Lys-Gly-Asp-Thr-Glu-Val-Met-Lys-Cys-Ile -Val-Glu-Val-Ile-Ser-Asp-Thr-Leu-Ser-Lys-Pro-Ser-Pro -Met-Pro-Val-Ser-Lys-Glu-Cys-Phe-Glu-D-Thr (SEQ ID NO:1);

(j1) Met-Asn-Lys-Gly-Asp-Thr-Glu-Val-Met-Lys-Cys-Ile-Val -Glu-Val-Ile-Ser-Asp-Thr-Leu-Ser-Lys-Pro-Ser-Pro-Met -Pro-Val-Ser-Lys-Glu-Cys-Phe-Glu (SEQ ID NO:1);

(j2) acetyl-Met-Asn-Lys-Gly-Asp-Thr-Glu-Val-Met-Lys-Cys -Ile-Val-Glu-Val-Ile-Ser-Asp-Thr-Leu-Ser-Lys-Pro-Ser -Pro-Met-Pro-Val-Ser-Lys-Glu-Cys-Phe-Glu (SEQ ID NO:1);

(j3) Met-Asn-Lys-Gly-Asp-Thr-Glu-Val-Met-Lys-Cys-Ile-Val -Glu-Val-Ile-Ser-Asp-Thr-Leu-Ser-Lys-Pro-Ser-Pro-Met -Pro-Val-Ser-Lys-Glu-Cys-Phe-Glu-D-Thr (SEQ ID NO:1);

(j4) acetyl-Met-Asn-Lys-Gly-Asp-Thr-Glu-Val-Met-Lys-Cys -Ile-Val-Glu-Val-Ile-Ser-Asp-Thr-Leu-Ser-Lys-Pro-Ser -Pro-Met-Pro-Val-Ser-Lys-Glu-Cys-Phe-Glu-D-Thr (SEQ ID NO:1);

(k1) Pro-Met-Asn-Lys-Gly-Asp-Thr-Glu-Val-Met-Lys-Cys-Ile -Val-Glu-Val-Ile-Ser-Asp-Thr-Leu-Ser-Lys-Pro-Ser-Pro -Met-Pro-Val-Ser-Lys-Glu-Cys-Phe-Glu (SEQ ID NO:1);

(k2) acetyl-Pro-Met-Asn-Lys-Gly-Asp-Thr-Glu-Val-Met-Lys -Cys-Ile-Val-Glu-Val-Ile-Ser-Asp-Thr-Leu-Ser-Lys-Pro -Ser-Pro-Met-Pro-Val-Ser-Lys-Glu-Cys-Phe-Glu (SEQ ID NO:1);

(k3) Pro-Met-Asn-Lys-Gly-Asp-Thr-Glu-Val-Met-Lys-Cys-Ile -Val-Glu-Val-Ile-Ser-Asp-Thr-Leu-Ser-Lys-Pro-Ser-Pro -Met-Pro-Val-Ser-Lys-Glu-Cys-Phe-Glu-D-Thr (SEQ ID NO:1);

(k4) acetyl-Pro-Met-Asn-Lys-Gly-Asp-Thr-Glu-Val-Met-Lys -Cys-Ile-Val-Glu-Val-Ile-Ser-Asp-Thr-Leu-Ser-Lys-Pro -Ser-Pro-Met-Pro-Val-Ser-Lys-Glu-Cys-Phe-Glu-D-Thr (SEQ ID NO:1).

14. The method of claim 11, wherein the peptide has the amino acid sequence:

X-Cys-Ile-Val-Glu-Val-Ile-Ala-Asp-Ala-Leu-Ala-Lys-Pro-Ala -Pro-Met-Pro-Val-Ala-Lys-Glu-Cys-Y (SEQ ID NO:1).

wherein:

X is X1 or acetyl-X1, wherein X1 is:
Lys-,
Met-Lys-,
Val-Met-Lys-,
Glu-Val-Met-Lys-,
Thr-Glu-Val-Met-Lys-,
Asp-Thr-Glu-Val-Met-Lys-,
Gly-Asp-Thr-Glu-Val-Met-Lys-,
Lys-Gly-Asp-Thr-Glu-Val-Met-Lys-,
Asn-Lys-Gly-Asp-Thr-Glu-Val-Met-Lys-,
Met-Asn-Lys-Gly-Asp-Thr-Glu-Val-Met-Lys-, or
Pro-Met-Asn-Lys-Gly-Asp-Thr-Glu-Val-Met-Lys-; and Y is -Phe-Glu or -Phe-Glu-D-Thr.

15. The method of claim 14, wherein the peptide has the amino acid selected from the group consisting of:

(a1) Lys-Cys-Ile-Val-Glu-Val-Ile-Ala-Asp-Ala-Leu-Ala-Lys -Pro-Ala-Pro-Met-Pro-Val-Ala-Lys-Glu-Cys-Phe-Glu (SEQ ID NO:1);

(a2) acetyl-Lys-Cys-Ile-Val-Glu-Val-Ile-Ala-Asp-Ala-Leu -Ala-Lys-Pro-Ala-Pro-Met-Pro-Val-Ala-Lys-Glu-Cys-Phe -Glu (SEQ ID NO:1);

(a3) Lys-Cys-Ile-Val-Glu-Val-Ile-Ala-Asp-Ala-Leu-Ala-Lys -Pro-Ala-Pro-Met-Pro-Val-Ala-Lys-Glu-Cys-Phe-Glu-D-Thr (SEQ ID NO:1);

(a4) acetyl-Lys-Cys-Ile-Val-Glu-Val-Ile-Ala-Asp-Ala-Leu -Ala-Lys-Pro-Ala-Pro-Met-Pro-Val-Ala-Lys-Glu-Cys-Phe -Glu-D-Thr (SEQ ID NO:1);

(b1) Met-Lys-Cys-Ile-Val-Glu-Val-Ile-Ala-Asp-Ala-Leu-Ala -Lys-Pro-Ala-Pro-Met-Pro-Val-Ala-Lys-Glu-Cys-Phe-Glu (SEQ ID NO:1);

(b2) acetyl-Met-Lys-Cys-Ile-Val-Glu-Val-Ile-Ala-Asp-Ala -Leu-Ala-Lys-Pro-Ala-Pro-Met-Pro-Val-Ala-Lys-Glu-Cys -Phe-Glu (SEQ ID NO:1);

(b3) Met-Lys-Cys-Ile-Val-Glu-Val-Ile-Ala-Asp-Ala-Leu-Ala -Lys-Pro-Ala-Pro-Met-Pro-Val-Ala-Lys-Glu-Cys-Phe-Glu-D -Thr (SEQ ID NO:1);

(b4) acetyl-Met-Lys-Cys-Ile-Val-Glu-Val-Ile-Ala-Asp-Ala -Leu-Ala-Lys-Pro-Ala-Pro-Met-Pro-Val-Ala-Lys-Glu-Cys -Phe-Glu-D-Thr (SEQ ID NO:1);

(c1) Val-Met-Lys-Cys-Ile-Val-Glu-Val-Ile-Ala-Asp-Ala-Leu -Ala-Lys-Pro-Ala-Pro-Met-Pro-Val-Ala-Lys-Glu-Cys-Phe -Glu (SEQ ID NO:1);

(c2) acetyl-Val-Met-Lys-Cys-Ile-Val-Glu-Val-Ile-Ala-Asp -Ala-Leu-Ala-Lys-Pro-Ala-Pro-Met-Pro-Val-Ala-Lys-Glu -Cys-Phe-Glu (SEQ ID NO:1);

(c3) Val-Met-Lys-Cys-Ile-Val-Glu-Val-Ile-Ala-Asp-Ala-Leu -Ala-Lys-Pro-Ala-Pro-Met-Pro-Val-Ala-Lys-Glu-Cys-Phe -Glu-D-Thr (SEQ ID NO:1);

(c4) acetyl-Val-Met-Lys-Cys-Ile-Val-Glu-Val-Ile-Ala-Asp -Ala-Leu-Ala-Lys-Pro-Ala-Pro-Met-Pro-Val-Ala-Lys-Glu -Cys-Phe-Glu-D-Thr (SEQ ID NO:1);

(d1) Glu-Val-Met-Lys-Cys-Ile-Val-Glu-Val-Ile-Ala-Asp-Ala -Leu-Ala-Lys-Pro-Ala-Pro-Met-Pro-Val-Ala-Lys-Glu-Cys -Phe-Glu (SEQ ID NO:1);

(d2) acetyl-Glu-Val-Met-Lys-Cys-Ile-Val-Glu-Val-Ile-Ala -Asp-Ala-Leu-Ala-Lys-Pro-Ala-Pro-Met-Pro-Val-Ala-Lys -Glu-Cys-Phe-Glu (SEQ ID NO:1);

(d3) Glu-Val-Met-Lys-Cys-Ile-Val-Glu-Val-Ile-Ala-Asp-Ala -Leu-Ala-Lys-Pro-Ala-Pro-Met-Pro-Val-Ala-Lys-Glu-Cys -Phe-Glu-D-Thr (SEQ ID NO:1);

(d4) acetyl-Glu-Val-Met-Lys-Cys-Ile-Val-Glu-Val-Ile-Ala -Asp-Ala-Leu-Ala-Lys-Pro-Ala-Pro-Met-Pro-Val-Ala-Lys -Glu-Cys-Phe-Glu-D-Thr (SEQ ID NO:1);

(e1) Thr-Glu-Val-Met-Lys-Cys-Ile-Val-Glu-Val-Ile-Ala-Asp -Ala-Leu-Ala-Lys-Pro-Ala-Pro-Met-Pro-Val-Ala-Lys-Glu -Cys-Phe-Glu (SEQ ID NO:1);

(e2) acetyl-Thr-Glu-Val-Met-Lys-Cys-Ile-Val-Glu-Val-Ile -Ala-Asp-Ala-Leu-Ala-Lys-Pro-Ala-Pro-Met-Pro-Val-Ala -Lys-Glu-Cys-Phe-Glu (SEQ ID NO:1);

(e3) Thr-Glu-Val-Met-Lys-Cys-Ile-Val-Glu-Val-Ile-Ala-Asp -Ala-Leu-Ala-Lys-Pro-Ala-Pro-Met-Pro-Val-Ala-Lys-Glu -Cys-Phe-Glu-D-Thr (SEQ ID NO:1);

(e4) acetyl-Thr-Glu-Val-Met-Lys-Cys-Ile-Val-Glu-Val-Ile -Ala-Asp-Ala-Leu-Ala-Lys-Pro-Ala-Pro-Met-Pro-Val-Ala -Lys-Glu-Cys-Phe-Glu-D-Thr (SEQ ID NO:1);

(f1) Asp-Thr-Glu-Val-Met-Lys-Cys-Ile-Val-Glu-Val-Ile-Ala -Asp-Ala-Leu-Ala-Lys-Pro-Ala-Pro-Met-Pro-Val-Ala-Lys -Glu-Cys-Phe-Glu (SEQ ID NO:1);

(f2) acetyl-Asp-Thr-Glu-Val-Met-Lys-Cys-Ile-Val-Glu-Val -Ile-Ala-Asp-Ala-Leu-Ala-Lys-Pro-Ala-Pro-Met-Pro-Val -Ala-Lys-Glu-Cys-Phe-Glu (SEQ ID NO:1);

(f3) Asp-Thr-Glu-Val-Met-Lys-Cys-Ile-Val-Glu-Val-Ile-Ala -Asp-Ala-Leu-Ala-Lys-Pro-Ala-Pro-Met-Pro-Val-Ala-Lys -Glu-Cys-Phe-Glu-D-Thr (SEQ ID NO:1);

(f4) acetyl-Asp-Thr-Glu-Val-Met-Lys-Cys-Ile-Val-Glu-Val -Ile-Ala-Asp-Ala-Leu-Ala-Lys-Pro-Ala-Pro-Met-Pro-Val -Ala-Lys-Glu-Cys-Phe-Glu-D-Thr (SEQ ID NO:1);

(g1) Gly-Asp-Thr-Glu-Val-Met-Lys-Cys-Ile-Val-Glu-Val-Ile -Ala-Asp-Ala-Leu-Ala-Lys-Pro-Ala-Pro-Met-Pro-Val-Ala -Lys-Glu-Cys-Phe-Glu (SEQ ID NO:1);

(g2) acetyl-Gly-Asp-Thr-Glu-Val-Met-Lys-Cys-Ile-Val-Glu -Val-Ile-Ala-Asp-Ala-Leu-Ala-Lys-Pro-Ala-Pro-Met-Pro -Val-Ala-Lys-Glu-Cys-Phe-Glu (SEQ ID NO:1);

(g3) Gly-Asp-Thr-Glu-Val-Met-Lys-Cys-Ile-Val-Glu-Val-Ile -Ala-Asp-Ala-Leu-Ala-Lys-Pro-Ala-Pro-Met-Pro-Val-Ala -Lys-Glu-Cys-Phe-Glu-D-Thr (SEQ ID NO:1);

(g4) acetyl-Gly-Asp-Thr-Glu-Val-Met-Lys-Cys-Ile-Val-Glu -Val-Ile-Ala-Asp-Ala-Leu-Ala-Lys-Pro-Ala-Pro-Met-Pro -Val-Ala-Lys-Glu-Cys-Phe-Glu-D-Thr (SEQ ID NO:1);

(h1) Lys-Gly-Asp-Thr-Glu-Val-Met-Lys-Cys-Ile-Val-Glu-Val -Ile-Ala-Asp-Ala-Leu-Ala-Lys-Pro-Ala-Pro-Met-Pro-Val -Ala-Lys-Glu-Cys-Phe-Glu (SEQ ID NO:1);

(h2) acetyl-Lys-Gly-Asp-Thr-Glu-Val-Met-Lys-Cys-Ile-Val -Glu-Val-Ile-Ala-Asp-Ala-Leu-Ala-Lys-Pro-Ala-Pro-Met -Pro-Val-Ala-Lys-Glu-Cys-Phe-Glu (SEQ ID NO:1);

(h3) Lys-Gly-Asp-Thr-Glu-Val-Met-Lys-Cys-Ile-Val-Glu-Val -Ile-Ala-Asp-Ala-Leu-Ala-Lys-Pro-Ala-Pro-Met-Pro-Val -Ala-Lys-Glu-Cys-Phe-Glu-D-Thr (SEQ ID NO:1);

(h4) acetyl-Lys-Gly-Asp-Thr-Glu-Val-Met-Lys-Cys-Ile-Val -Glu-Val-Ile-Ala-Asp-Ala-Leu-Ala-Lys-Pro-Ala-Pro-Met -Pro-Val-Ala-Lys-Glu-Cys-Phe-Glu-D-Thr (SEQ ID NO:1);

(i1) Asn-Lys-Gly-Asp-Thr-Glu-Val-Met-Lys-Cys-Ile-Val-Glu -Val-Ile-Ala-Asp-Ala-Leu-Ala-Lys-Pro-Ala-Pro-Met-Pro -Val-Ala-Lys-Glu-Cys-Phe-Glu (SEQ ID NO:1);

(i2) acetyl-Asn-Lys-Gly-Asp-Thr-Glu-Val-Met-Lys-Cys-Ile -Val-Glu-Val-Ile-Ala-Asp-Ala-Leu-Ala-Lys-Pro-Ala-Pro -Met-Pro-Val-Ala-Lys-Glu-Cys-Phe-Glu (SEQ ID NO:1);

(i3) Asn-Lys-Gly-Asp-Thr-Glu-Val-Met-Lys-Cys-Ile-Val-Glu -Val-Ile-Ala-Asp-Ala-Leu-Ala-Lys-Pro-Ala-Pro-Met-Pro -Val-Ala-Lys-Glu-Cys-Phe-Glu-D-Thr (SEQ ID NO:1);

(i4) acetyl-Asn-Lys-Gly-Asp-Thr-Glu-Val-Met-Lys-Cys-Ile -Val-Glu-Val-Ile-Ala-Asp-Ala-Leu-Ala-Lys-Pro-Ala-Pro -Met-Pro-Val-Ala-Lys-Glu-Cys-Phe-Glu-D-Thr (SEQ ID NO:1);

(j1) Met-Asn-Lys-Gly-Asp-Thr-Glu-Val-Met-Lys-Cys-Ile-Val -Glu-Val-Ile-Ala-Asp-Ala-Leu-Ala-Lys-Pro-Ala-Pro-Met -Pro-Val-Ala-Lys-Glu-Cys-Phe-Glu (SEQ ID NO:1);

(j2) acetyl-Met-Asn-Lys-Gly-Asp-Thr-Glu-Val-Met-Lys-Cys -Ile-Val-Glu-Val-Ile-Ala-Asp-Ala-Leu-Ala-Lys-Pro-Ala -Pro-Met-Pro-Val-Ala-Lys-Glu-Cys-Phe-Glu (SEQ ID NO: 1);

(j3) Met-Asn-Lys-Gly-Asp-Thr-Glu-Val-Met-Lys-Cys-Ile-Val -Glu-Val-Ile-Ala-Asp-Ala-Leu-Ala-Lys-Pro-Ala-Pro-Met -Pro-Val-Ala-Lys-Glu-Cys-Phe-Glu-D-Thr (SEQ ID NO:1);

(j4) acetyl-Met-Asn-Lys-Gly-Asp-Thr-Glu-Val-Met-Lys-Cys -Ile-Val-Glu-Val-Ile-Ala-Asp-Ala-Leu-Ala-Lys-Pro-Ala -Pro-Met-Pro-Val-Ala-Lys-Glu-Cys-Phe-Glu-D-Thr (SEQ ID NO:1);

(k1) Pro-Met-Asn-Lys-Gly-Asp-Thr-Glu-Val-Met-Lys-Cys- Ile -Val-Glu-Val-Ile-Ala-Asp-Ala-Leu-Ala-Lys-Pro-Ala-Pro -Met-Pro-Val-Ala-Lys-Glu-Cys-Phe-Glu (SEQ ID NO:1);

(k2) acetyl-Pro-Met-Asn-Lys-Gly-Asp-Thr-Glu-Val-Met-Lys -Cys-Ile-Val-Glu-Val-Ile-Ala-Asp-Ala-Leu-Ala-Lys-Pro -Ala-Pro-Met-Pro-Val-Ala-Lys-Glu-Cys-Phe-Glu (SEQ ID NO:1);

(k3) Pro-Met-Asn-Lys-Gly-Asp-Thr-Glu-Val-Met-Lys-Cys-Ile -Val-Glu-Val-Ile-Ala-Asp-Ala-Leu-Ala-Lys-Pro-Ala-Pro -Met-Pro-Val-Ala-Lys-Glu-Cys-Phe-Glu-D-Thr (SEQ ID NO:1); and (k4) acetyl-Pro-Met-Asn-Lys-Gly-Asp-Thr-Glu-Val-Met-Lys -Cys-Ile-Val-Glu-Val-Ile-Ala-Asp-Ala-Leu-Ala-Lys-Pro -Ala-Pro-Met-Pro-Val-Ala-Lys-Glu-Cys-Phe-Glu-D-Thr (SEQ ID NO:1).

16. The method of claim 11, wherein the subject has hyperparathyroidism.

17. The method of claim 11, wherein the subject has osteoporosis.

* * * * *

SEQUENCE LISTING ( 1 ) GENERAL INFORMATION:

( i i i ) NUMBER OF SEQUENCES: 2

( 2 ) INFORMATION FOR SEQ ID NO:1:

( i ) SEQUENCE CHARACTERISTICS:
        ( A ) LENGTH: 37
        ( B ) TYPE: amino acid
        ( D ) TOPOLOGY: linear ( i i ) MOLECULE TYPE:
        ( A ) DESCRIPTION: peptide ( i i i ) HYPOTHETICAL: NO ( v i ) ORIGINAL SOURCE:
        ( A ) ORGANISM:
        ( B ) INDIVIDUAL ISOLATE: chromogranin A ( i x ) FEATURE:
        ( D ) OTHER INFORMATION: Xaa at 1 is acetyl or nothing;
        Xaa at 13 and 34 is cysteine or lanthionine; Xaa
        at 19, 23, 26 and 31 is serine or alanine; Xaa at
        21 is threonine or alanine; Xaa at 37 is D-
        threonine; 2-11 may be deleted.

( x i ) SEQUENCE DESCRIPTION: SEQ ID NO:1:

Xaa Pro Met Asn Lys Gly Asp Thr Glu Val Met Lys Xaa Ile
1                    5                          10

```
Val Glu Val Ile Xaa Asp Xaa Leu Xaa Lys Pro Xaa Pro Met
 15              20              25
```

```
Pro Val Xaa Lys Glu Xaa Phe Glu Xaa
     30          35
```

( 2 ) INFORMATION FOR SEQ ID NO:2:

( i ) SEQUENCE CHARACTERISTICS:
       ( A ) LENGTH: 40
       ( B ) TYPE: amino acid
       ( D ) TOPOLOGY: linear ( i i ) MOLECULE TYPE:
       ( A ) DESCRIPTION: peptide ( i i i ) HYPOTHETICAL: NO ( v i ) ORIGINAL SOURCE:
       ( A ) ORGANISM:
       ( B ) INDIVIDUAL ISOLATE: chromogranin A ( x i ) SEQUENCE DESCRIPTION: SEQ ID NO:2:

```
Leu Pro Val Asn Ser Pro Met Asn Lys Gly Asp Thr Glu Val
 1            5                  10
```

```
Met Lys Cys Ile Val Glu Val Ile Ser Asp Thr Leu Ser Lys
 15              20              25
```

```
Pro Ser Pro Met Pro Val Ser Lys Glu Cys Phe Glu
     30              35              40
```